(12) United States Patent
Jensen et al.

(10) Patent No.: US 10,269,368 B2
(45) Date of Patent: Apr. 23, 2019

(54) AUDIO PROCESSING DEVICE AND A METHOD FOR ESTIMATING A SIGNAL-TO-NOISE-RATIO OF A SOUND SIGNAL

(71) Applicant: Oticon A/S, Smørum (DK)

(72) Inventors: Jesper Jensen, Smørum (DK); Ulrik Kjems, Frederiksberg C (DK); Andreas Thelander Bertelsen, Smørum (DK); Michael Syskind Pedersen, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 15/608,224

(22) Filed: May 30, 2017

(65) Prior Publication Data

US 2017/0345439 A1 Nov. 30, 2017
US 2018/0233160 A9 Aug. 16, 2018

Related U.S. Application Data

(63) Continuation-in-part of application No. 15/318,046, filed as application No. PCT/EP2015/062924 on Jun. 10, 2015, now Pat. No. 10,109,290.

(30) Foreign Application Priority Data

Jun. 13, 2014 (EP) ..................................... 14172412
May 30, 2016 (EP) ..................................... 16171986

(51) Int. Cl.
*G10L 15/20* (2006.01)
*G10L 21/0232* (2013.01)
(Continued)

(52) U.S. Cl.
CPC ...... *G10L 21/0232* (2013.01); *G10L 21/0264* (2013.01); *H04R 1/1083* (2013.01);
(Continued)

(58) Field of Classification Search
CPC .. G10L 21/0232; G10L 21/0216; G10L 25/84
(Continued)

(56) References Cited

U.S. PATENT DOCUMENTS 6,098,038 A 8/2000 Hermansky et al.
7,058,572 B1 6/2006 Nemer
(Continued)

FOREIGN PATENT DOCUMENTS

WO WO 2015/189261 A1 12/2015

OTHER PUBLICATIONS

Breithaupt et al., "Analysis of the Decision-Directed SNR Estimator for Speech Enhancement With Respect to Low-SNR and Transient Conditions," IEEE Transactions on Audio, Speech, and Language Processing, Apr. 8, 2010, pp. 277-289.
(Continued)

*Primary Examiner* — Paul Kim
*Assistant Examiner* — Ubachukwu A Odunukwe
(74) *Attorney, Agent, or Firm* — Birch, Stewart, Kolasch & Birch, LLP

(57) ABSTRACT

An audio processing device comprises a) at least one input unit for providing time-frequency representation Y(k,n) of an electric input signal representing sound consisting of target speech and noise signal components, where k and n are frequency band and time frame indices, respectively, b) a noise detection and/or reduction system configured to b1) determine an a posteriori signal to noise ratio estimate γ(k,n) of said electric input signal, and to b2) determine an a priori target signal to noise signal ratio estimate ζ(k,n) of said electric input signal from said a posteriori signal to noise ratio estimate γ(k,n) based on a recursive decision directed algorithm. The application further relates to a method of of estimating an a priori signal to noise ratio. The invention may e.g. be used for the hearing aids, headsets, ear phones,
(Continued)

active ear protection systems, handsfree telephone systems, mobile telephones, etc.

23 Claims, 14 Drawing Sheets

(51) Int. Cl.
| | |
|---|---|
| *H04R 1/10* | (2006.01) |
| *G10L 21/0264* | (2013.01) |
| *H04R 25/00* | (2006.01) |
| *G10L 21/0216* | (2013.01) |
| *A61F 11/06* | (2006.01) |
| *H04B 1/3827* | (2015.01) |
| *H04M 1/60* | (2006.01) |

(52) U.S. Cl.
CPC ............ *H04R 25/505* (2013.01); *A61F 11/06* (2013.01); *G10L 21/0216* (2013.01); *H04B 1/3833* (2013.01); *H04M 1/6041* (2013.01); *H04R 25/50* (2013.01); *H04R 25/558* (2013.01); *H04R 2225/43* (2013.01)

(58) Field of Classification Search
USPC ............ 381/94.1, 71.1, 71.11; 704/233, 205, 704/E15.039, 226, 500
See application file for complete search history.

(56) References Cited

U.S. PATENT DOCUMENTS

| | | | |
|---|---|---|---|
| 8,244,523 B1* | 8/2012 | Murphy ................. | G10L 25/84 381/71.11 |
| 8,521,530 B1 | 8/2013 | Every et al. | |
| 2009/0119111 A1 | 5/2009 | Goto et al. | |
| 2012/0158404 A1* | 6/2012 | Shin .................... | G10L 21/0216 704/233 |
| 2013/0191118 A1 | 7/2013 | Makino | |
| 2014/0056435 A1* | 2/2014 | Kjems .................... | G10L 15/20 381/66 |
| 2015/0142425 A1 | 5/2015 | Sjoberg et al. | |

OTHER PUBLICATIONS

Martin, "Noise Power Spectral Density Estimation Based on Optimal Smoothing and Minimum Statistics," IEEE Transactions on Speech and Audio Processing, vol. 9, No. 5, Jul. 2001, pp. 504-512.

Ephraim et al., "Speech Enhancement Using a Minimum Mean-Square Error Short-Time Spectral Amplitude Estimator", IEEE Transactions on Acoustics, Speech, and Signal Processing, vol. ASSP-32, No. 6, Dec. 1984, pp. 1109-1121.

Ephraim et al., "Speech Enhancement Using a Minimum Mean-Square Error Log-Spectral Amplitude Estimator", IEEE Transactions on Acoustics, Speech, and Signal Processing, vol. ASSP-33, No. 2, Apr. 1985, pp. 443-445.

Erkelens et al., "Minimum Mean-Square Error Estimation of Discrete Fourier Coefficients With Generalized Gamma Priors", IEEE Transactions on Audio, Speech, and Language Processing, vol. 15, No. 6. Aug. 2007, pp. 1741-1752.

Hamacher et al., "Signal Processing in High-End Hearing Aids: State of the Art, Challenges, and Future Trends", EURASIP Journal on Applied Signal Processing 2005, No. 18, 2005, pp. 2915-2929.

Loizou, Philipos C. "Speech Enhancement: Theory and Practice". CRC Press, Inc., Boca Raton, FL., USA, 711 pgs. (2013). ISBN: 1466504218 9781466504219. Abstract Only.

Olivier Cappe, "Elimination of the Musical Noise Phenomenon with the Ephraim and Malah Noise Suppressor." IEEE Transactions on Speech and Processing, vol. 2, No. 2, pp. 345-349 (Apr. 1994).

* cited by examiner

AUDIO PROCESSING DEVICE AND A METHOD FOR ESTIMATING A SIGNAL-TO-NOISE-RATIO OF A SOUND SIGNAL

CROSS REFERENCE TO RELATED APPLICATIONS

This application is a Continuation-In-Part of copending application Ser. No. 15/318,046, filed on Dec. 12, 2016, which is a National Phase of PCT International Application No. PCT/EP2015/062924 filed on Jun. 10, 2015. This application claims priority of Application Nos. EP 14172412.0 and EP16171986.9, filed in Europe on Jun. 13, 2014 and May 30, 2016, respectively.

SUMMARY

The present disclosure relates to an audio processing device, e.g. a hearing aid, and a method for estimating a signal to noise ratio of an electric input signal representing sound. The disclosure relates specifically to a scheme for obtaining an a priori (or second) signal-to-noise-ratio estimate by non-linear smoothing (e.g. implemented as low pass filtering with adaptive cut-low pass off frequency) of an a posteriori (or first) signal-to-noise-ratio estimate.

In the present context 'an a posteriori signal to noise ratio', $SNR_{post}$, is taken to mean a ratio between the observed (available) noisy signal (target signal S plus noise N, $Y(t)=S(t)+N(t)$), e.g. a picked up by one or more microphones, such as the power of the noisy signal, and the noise $N(t)$, such as an estimate ($\hat{N}(t)$) of the noise, such as the power of the noise signal, at a given point in time t, i.e. $SNR_{post}(t)=Y(t)/\hat{N}(t)$, or $SNR_{post}(t)=Y(t)^2/\hat{N}(t)^2$. The 'a posteriori signal to noise ratio', $SNR_{post}$, may e.g. be defined in the time-frequency domain as a value for each frequency band (index k) and time frame (index n), i.e. $SNR_{post}=SNR_{post}(k,n)$, i.e. e.g. $SNR_{post}(k,n)=|Y(k,n)|^2/|\hat{N}(k,n)|^2$. Examples of the generation of an 'a posteriori' signal to noise ratio are illustrated in FIGS. 1A and 1B for a one-microphone and a multi-microphone setup, respectively.

In the present context 'an a priori signal to noise ratio' $SNR_{prio}$ is taken to mean a ratio of the target signal amplitude $S(t)$ (or of the target signal power $S(t)^2$) to the noise signal amplitude $N(t)$ (or to the noise signal power $N(t)^2$), respectively, such as a ratio between estimates of these signals at a given point in time t, e.g. $SNR_{prio}=SNR_{prio}(t)=\hat{S}(t)^2/\hat{N}(t)^2$, or $SNR_{prio}=SNR_{prio}(k,n)$, i.e. e.g. $SNR_{prio}(k,n)=|\hat{S}(k,n)|^2/|\hat{N}(k,n)|^2$.

An Audio Processing Device, e.g. a Hearing Device, Such as a Hearing Aid:

In a first aspect of the present application, an audio processing device is provided. The audio processing device, e.g. a hearing aid, comprises at least one input unit for providing a time-frequency representation Y(k,n) of an electric input signal representing a time variant sound signal consisting of target speech signal components S(k,n) from a target sound source TS and noise signal components N(k,n), where k and n are frequency band and time frame indices, respectively, a noise reduction system configured to
determine a first, a posteriori, signal to noise ratio estimate γ(k,n) of said electric input signal, and to
determine a second, a priori, target signal to noise ratio estimate ζ(k,n) of said electric input signal from said a posteriori signal to noise ratio estimate γ(k,n) based on a recursive algorithm, and to
determine said a priori target signal to noise ratio estimate ζ(k,n) for the $n^{th}$ timeframe from
said a priori target signal to noise ratio estimate ζ(k,n−1) for the $(n-1)^{th}$ timeframe, and from
said a posteriori signal to noise ratio estimate γ(k,n) for the $n^{th}$ timeframe.

In an embodiment, the recursive algorithm is configured to implement a low pass filter with an adaptive time constant. In an embodiment, the noise reduction system comprises the low pass filter. In an embodiment, the recursive algorithm implements a $1^{st}$ order IIR low pass filter with unit DC-gain, and an adaptive time constant (or low-pass cut-off frequency).

In a second aspect of the present application, an audio processing device is provided. The audio processing device, e.g. a hearing aid, comprises at least one input unit for providing a time-frequency representation Y(k,n) of an electric input signal representing a time variant sound signal consisting of target speech signal components S(k,n) from a target sound source TS and noise signal components N(k,n), where k and n are frequency band and time frame indices, respectively, a noise reduction system configured for each frequency band to
determine a first, a posteriori, signal to noise ratio estimate γ(k,n) of said electric input signal, and to
determine a second, a priori, target signal to noise ratio estimate ζ(k,n) of said electric input signal from said a posteriori signal to noise ratio estimate γ(k,n) based on a recursive algorithm, wherein said recursive algorithm implements a low pass filter with an adaptive time constant or low-pass cut-off frequency.

In other words, the second, a priori, target signal to noise ratio estimate ζ(k,n) is determined by low pass filtering the first, a posteriori, signal to noise ratio estimate γ(k,n).

In an embodiment, the adaptive time constant or low-pass cut-off frequency of the low pass filter is determined in dependence of the first, a posteriori, and/or the second, a priori, signal to noise ratio estimates.

In an embodiment, the adaptive time constant or low-pass cut-off frequency of the low pass filter for a given frequency index k (also termed frequency channel k) is determined in dependence of the first, a posteriori, and/or the second, a priori, signal to noise ratio estimates solely corresponding to that frequency index k.

In an embodiment, the adaptive time constant or low-pass cut-off frequency of the low pass filter for a given frequency index k (also termed frequency channel k) is determined in dependence of the first, a posteriori, and/or the second, a priori, signal to noise ratio estimates corresponding to a number of frequency indices k', e.g. at least including neighboring frequency indices k−1, k, k+1, e.g. according to a predefined (or adaptive) scheme.

In an embodiment, the adaptive time constant or low-pass cut-off frequency of the low pass filter for a given frequency index k (also termed frequency channel k) is determined in dependence of inputs from one or more detectors (e.g. onset indicators, wind noise or voice detectors, etc.).

In an embodiment, the low pass filter is a $1^{st}$ order IIR low pass filter. In an embodiment, $1^{st}$ order IIR low pass filter has unit DC-gain.

In an embodiment, the adaptive time constant or low-pass cut-off frequency of the low pass filter at a given time instant n is determined in dependence of a first maximum likelihood estimate of the second, a priori, target signal to noise ratio estimate at that time instant n and/or an estimate of the second, a priori, target signal to noise ratio estimate at the previous time instant n−1.

Thereby an improved noise reduction may be provided.

The noise signal components N(k,n) may e.g. originate from one or more other sources $NS_i$ (i=1, ..., $N_s$) than the target sound source TS. In an embodiment, the noise signal components N(k,n) include late reverberations from the target signal (e.g. target signal components that arrive at the user more than 50 ms later than the dominant peak of the target signal component in question).

In other words, ζ(k,n)=F(ζ(k,n−1), γ(k,n)). Using the most recent frame power for the a posteriori SNR (SNR=Signal to Noise Ratio) in the determination of the a priori SNR may e.g. be beneficial for SNR estimation at speech onsets, where large increases to the SNR typically occur over a short time.

In an embodiment, the noise reduction system is configured to determine said a priori target signal to noise ratio estimate ζ(k,n) for the $n^{th}$ time frame under the assumption that γ(k,n) is larger than or equal to 1. In an embodiment, the a posteriori signal to noise ratio estimate γ(k,n) of the electric input signal Y(k,n) is e.g. defined as the ratio between a signal power spectral density $|Y(k,n)|^2$ of the current value Y(k,n) of the electric input signal and an estimate $\langle\sigma^2\rangle$ of the current noise power spectral density of the electric input signal Y(k,n), i.e. $\gamma(k,n)=|Y(k,n)|^2/\langle\sigma^2\rangle$.

In an embodiment, the noise reduction system is configured to determine said a priori target signal to noise ratio estimate ζ(k,n) for the $n^{th}$ timeframe from said a priori target signal to noise ratio estimate ζ(k,n−1) for the $(n-1)^{th}$ timeframe, and from the maximum likelihood SNR estimator $\zeta^{ML}(k,n)$ of the a priori target signal to noise ratio estimate ζ(k,n) for the $n^{th}$ timeframe.

In an embodiment, the noise reduction system is configured to determine said maximum likelihood SNR estimator $\zeta^{ML}(k,n)$ as MAX$\{\zeta^{ML}_{min}(k,n); \gamma(k,n)-1\}$, where MAX is the maximum operator, and $\zeta^{ML}_{min}(k,n)$ is a minimum value of the maximum likelihood SNR estimator $\zeta^{ML}(k,n)$. In an embodiment, the minimum value $\zeta^{ML}_{min}(k,n)$ of the maximum likelihood SNR estimator $\zeta^{ML}(k,n)$ may e.g. be dependent of frequency band index. In an embodiment, the minimum value $\zeta^{ML}_{min}(k,n)$ is independent. In an embodiment $\zeta^{ML}_{min}(k,n)$ is taken to be equal to '1' (i.e. =0 dB on a logarithmic scale). This is e.g. the case when the target signal components S(k,n) are negligible; i.e. when only noise components N(k,n) are present in the input signal Y(k,n)).

In an embodiment, the noise reduction system is configured to determine said a priori target signal to noise ratio estimate ζ by non-linear smoothing of said a posteriori signal to noise ratio estimate γ, or a parameter derived therefrom, wherein said non-linear smoothing is e.g. controlled by one or more bias and/or smoothing parameters. A parameter derived therefrom may e.g. be a processed version of the original parameter. A parameter derived therefrom may (in connection with the posteriori signal to noise ratio estimate γ) e.g. be the maximum likelihood SNR estimator $\zeta^{ML}$. The non-linear smoothing may e.g. be implemented by low pass filtering with adaptive cut-low pass off frequency, e.g. by a $1^{st}$ order IIR low pass filter with unit DC-gain, and an adaptive time constant.

In an embodiment, the noise reduction system is configured to provide an SNR-dependent smoothing, allowing for more smoothing in low SNR conditions than for high SNR conditions. This may have the advantage of reducing musical noise. The terms 'low SNR conditions' and 'high SNR conditions' are intended to indicate first and second conditions where the true SNR is lower under the first conditions than under the second conditions. In an embodiment, 'low SNR conditions' and 'high SNR conditions' are taken to mean below and above 0 dB, respectively. Preferably, the dependence a time constant controlling the smoothing exhibit a gradual change in dependence of SNR. In an embodiment, the time constant(s) involved in smoothing are higher the lower the SNR. At 'low SNR conditions', the SNR estimate is generally relatively poorer than at 'high SNR conditions' (and hence less trustworthy at lower SNR; and hence a driver for more smoothing).

In an embodiment, the noise reduction system is configured to provide a negative bias compared to $\xi_n^{ML}$ for low SNR conditions. This may have the advantage of reducing audibility of musical noise in noise-only periods. The term "bias" is in the present context used to reflect a difference between the expected value $E(\xi_n^{ML})$ of the maximum likelihood SNR estimator $\zeta^{ML}(k,n)$ and the expected value $E(\zeta_n)$ of the a priori signal to noise ratio ζ(k,n). In other words, for 'low SNR conditions' (e.g. for true SNR<0 dB), $E(\xi_n^{ML})-E(\zeta_n)<0$ (as e.g. reflected in FIG. 3).

In an embodiment, the noise reduction system is configured to provide a recursive bias, allowing a configurable change from low-to-high and high-to-low SNR conditions.

In a logarithmic representation of the a priori signal to noise ratio for the $n^{th}$ time frame may be expressed as $s_n=s(k,n)=10\log(\zeta(k,n))$ and correspondingly for the maximum likelihood SNR estimator for the $n^{th}$ time frame: $s^{ML}_n=s^{ML}(k,n)=10\log(\zeta^{ML}(k,n))$.

In an embodiment, the noise reduction system is configured to determine said a priori target signal to noise ratio estimate ζ(k,n) for the $n^{th}$ timeframe from said a priori target signal to noise ratio estimate ζ(k,n−1) for the $(n-1)^{th}$ timeframe, and from the maximum likelihood SNR estimator $\zeta^{ML}(k,n)$ of the a priori target signal to noise ratio estimate ζ(k,n) for the $n^{th}$ time frame according to the following recursive algorithm:

$$s_n - s_{n-1} = (s_n^{ML} + \rho(s_{n-1}) - s_{n-1})\lambda(s_{n-1})$$

where $\rho(s_{n-1})$ represents a bias function or parameter and $\lambda(s_{n-1})$ represents a smoothing function or parameter of the $(n-1)^{th}$ time frame.

In an embodiment, $\rho(s_{n-1})$ is chosen as to be equal to the value of $$10\log_{10}\frac{\xi}{\xi_{n-1}}$$

with ξ satisfying $$10\log_{10}\Psi\left(\xi_{n-1}, \frac{\xi}{\xi_{n-1}}\right) = 0 \text{ dB, where}$$

$$\Psi\left(\xi_{n-1}, \frac{\xi}{\xi_{n-1}}\right)$$

is a non-linear function as defined in equation (8).

In an embodiment, the smoothing function $\lambda(s_{n-1})$ is chosen to be equal to the slope (w.r.t. $s_n^{ML}$) of the function $$10\log_{10}\Psi\left(\xi_{n-1}, \frac{\xi}{\xi_{n-1}}\right) = 0 \text{ dB}$$

(cf. curves in FIG. 3) at the location of the 0 dB crossing (i.e. when $s_n^{ML} - s_n = \rho(s_{n-1})$).

In an embodiment, the audio processing device comprises a filter bank comprising an analysis filter bank for providing said time-frequency representation Y(k,n) of said electric input signal. In an embodiment, the electric input signal is available as a number of frequency sub-band signals Y(k,n), k=1, 2, . . . , K. In an embodiment, the a priori signal to noise ratio estimate $\zeta(k,n)$, depend on the a posteriori signal to noise ratio estimate $\gamma(k,n)$ in a neighboring frequency sub-band signal (e.g. on $\gamma(k-1,n)$ and/or $\gamma(k+1,n)$).

In an embodiment, the audio processing device is configured to provide that said analysis filter bank is oversampled. In an embodiment, the audio processing device is configured to provide that the analysis filter bank is a DFT-modulated analysis filter bank.

In an embodiment, the recursive loop of the algorithm for determining said a priori target signal to noise ratio estimate $\zeta(k,n)$ for the $n^{th}$ timeframe comprises a higher order delay element, e.g. a circular buffer. In an embodiment, the higher order delay element is configured to compensate for oversampling of the analysis filter bank.

In an embodiment, the noise reduction system is configured to adapt the algorithm for determining said a priori target signal to noise ratio estimate $\zeta(k,n)$ for the $n^{th}$ timeframe to compensate for oversampling of the analysis filter bank. In an embodiment, the algorithm comprises a smoothing parameter ($\lambda$) and/or a bias parameter ($\rho$).

In an embodiment, the two functions $\lambda$ and $\rho$ control the amount of smoothing and the amount of SNR bias, as a recursive function of the estimated SNR.

In an embodiment, the smoothing parameter ($\lambda$) and/or a bias parameter ($\rho$) are adapted to compensate for a sampling rate, see e.g. FIG. 5. In an embodiment, different oversampling rates are compensated for by adapting the parameter $\alpha$, cf. e.g. FIG. 8.

In an embodiment, the recursive algorithm comprises a recursive loop for recursively determining a (second) a priori SNR estimate from a (first) a posteriori SNR estimate.

In an embodiment, the audio processing device, e.g. the recursive algorithm, comprises a selector located in the recursive loop, allowing the maximum likelihood SNR estimator of the present time frame n to bypass the a priori estimate of the previous time frame n−1 in the calculation of said bias and smoothing parameters ($\rho$, $\lambda$), e.g. modified (e.g. off-set) by a bypass parameter $\kappa$.

In an embodiment, the selector is controlled by a select control parameter wherein the select control parameter for a given frequency index k is determined in dependence of the first, a posteriori, and/or the second, a priori, signal to noise ratio estimates corresponding to a number of frequency indices k', e.g. at least including neighboring frequency indices k−1, k, k+1, according to a predefined or adaptive scheme. In an embodiment, the select control parameter for a given frequency index k is (additionally or alternatively) determined in dependence of inputs from one or more detectors, e.g. an onset detector, a wind noise detector, a voice detector, or a combination thereof.

In an embodiment, the noise reduction system comprises an SNR to gain conversion unit providing a resulting current noise reduction gain $G_{NR}$ from the a priori SNR (e.g. based on a Wiener gain function). In an embodiment, the audio processing device comprises a combination unit for applying the current noise reduction gain to the electric input signal Y(n,k) (or a signal originating there from) to provide a noise reduced signal (cf. e.g. signal $Y_{NR}$ in FIG. 1A, 1B, or 9A, 9B).

In an embodiment, the audio processing device (e.g. a hearing aid) further comprises a synthesis filter bank for converting processed (e.g. noise reduced) frequency sub-band signals to a time domain output signal. In an embodiment, the time domain output signal is fed to an output unit for providing stimuli to a user as a signal perceivable as sound.

In an embodiment, the audio processing device comprises a hearing device, such as a hearing aid, a headset, an earphone, an ear protection device or a combination thereof.

In an embodiment, the audio processing device is adapted to provide a frequency dependent gain and/or a level dependent compression and/or a transposition (with or without frequency compression) of one or frequency ranges to one or more other frequency ranges, e.g. to compensate for a hearing impairment of a user and/or to compensate for challenging acoustic environment. In an embodiment, the audio processing device comprises a signal processing unit for enhancing the input signals and providing a processed output signal.

In an embodiment, the audio processing device comprises an output unit for providing a stimulus perceived by the user as an acoustic signal based on a processed electric signal. In an embodiment, the output unit comprises a number of electrodes of a cochlear implant or a vibrator of a bone conducting hearing device. In an embodiment, the output unit comprises an output transducer. In an embodiment, the output transducer comprises a receiver (loudspeaker) for providing the stimulus as an acoustic signal to the user. In an embodiment, the output transducer comprises a vibrator for providing the stimulus as mechanical vibration of a skull bone to the user (e.g. in a bone-attached or bone-anchored hearing device).

In an embodiment, the audio processing device comprises an input unit for providing an electric input signal representing sound. In an embodiment, the input unit comprises an input transducer, e.g. a microphone, for converting an input sound to an electric input signal. In an embodiment, the input unit comprises a wireless receiver for receiving a wireless signal comprising sound and for providing an electric input signal representing said sound.

In an embodiment, the audio processing device is portable device, e.g. a device comprising a local energy source, e.g. a battery, e.g. a rechargeable battery.

In an embodiment, an a priori SNR estimate of a given hearing aid that forms part of a binaural hearing aid system is based on a posteriori SNR estimates from both hearing aids of the binaural hearing aid system. In an embodiment, an a priori SNR estimate of a given hearing aid that forms part of a binaural hearing aid system is based on an a posteriori SNR estimate of the given hearing aid and an a priori SNR estimate of the other hearing aid of the binaural hearing aid system.

In an embodiment, the audio processing device comprises a forward (or signal) path between an input transducer (microphone system and/or direct electric input (e.g. a wireless receiver)) and an output transducer. In an embodiment, the signal processing unit is located in the forward path. In an embodiment, the signal processing unit is adapted to provide a frequency dependent gain according to a user's particular needs. In an embodiment, the audio processing device comprises an analysis (or control) path comprising functional components for analyzing the input signal (e.g. determining a level, a modulation, a type of signal, an acoustic feedback estimate, etc.), and possibly controlling processing of the forward path. In an embodiment, some or all signal processing of the analysis path and/or the signal path is conducted in the frequency domain. In an embodiment, some or all signal processing of the analysis path and/or the signal path is conducted in the time domain.

In an embodiment, the analysis (or control) path is operated in fewer channels (or frequency sub-bands) than the forward path. This can e.g. be done to save power in an audio processing device, such as a portable audio processing device, e.g. a hearing aid, where power consumption is an important parameter.

In an embodiment, an analogue electric signal representing an acoustic signal is converted to a digital audio signal in an analogue-to-digital (AD) conversion process, where the analogue signal is sampled with a predefined sampling frequency or rate $f_s$, $f_s$ being e.g. in the range from 8 kHz to 48 kHz (adapted to the particular needs of the application) to provide digital samples $x_n$ (or x[n]) at discrete points in time $t_n$ (or n), each audio sample representing the value of the acoustic signal at $t_n$ by a predefined number $N_s$ of bits, $N_s$ being e.g. in the range from 1 to 16 bits. A digital sample x has a length in time of $1/f_s$, e.g. 50 μs, for $f_s=20$ kHz. In an embodiment, a number of audio samples are arranged in a time frame. In an embodiment, a time frame comprises 64 or 128 audio data samples. Other frame lengths may be used depending on the practical application. In an embodiment, a frame is shifted every ms or every 2 ms in case of oversampling (e.g. in case a critical sampling (no frame overlap) corresponds to a frame length of 3.2 ms (e.g. for $f_s=20$ kHz, and 64 samples per frame)). In other words the frames overlap, so that a only a certain fraction of samples are new from a given frame to the next, e.g. 25% or 50% or 75% of the samples.

In an embodiment, the audio processing devices comprise an analogue-to-digital (AD) converter to digitize an analogue input with a predefined sampling rate, e.g. 20 kHz. In an embodiment, the audio processing devices comprise a digital-to-analogue (DA) converter to convert a digital signal to an analogue output signal, e.g. for being presented to a user via an output transducer.

In an embodiment, the audio processing device, e.g. the microphone unit, and or the transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the audio processing device from a minimum frequency $f_{min}$ to a maximum frequency $f_{max}$ comprises a part of the typical human audible frequency range from 20 Hz to 20 kHz, e.g. a part of the range from 20 Hz to 12 kHz. In an embodiment, a signal of the forward and/or analysis path of the audio processing device is split into a number NI of frequency bands, where NI is e.g. larger than 5, such as larger than 10, such as larger than 50, such as larger than 100, such as larger than 500, at least some of which are processed individually. In an embodiment, the audio processing device is/are adapted to process a signal of the forward and/or analysis path in a number NP of different frequency channels (NP≤NI). The frequency channels may be uniform or non-uniform in width (e.g. increasing in width with frequency), overlapping or non-overlapping.

In an embodiment, the audio processing device comprises a number of detectors configured to provide status signals relating to a current physical environment of the audio processing device (e.g. the current acoustic environment), and/or to a current state of the user wearing the audio processing device, and/or to a current state or mode of operation of the audio processing device. Alternatively or additionally, one or more detectors may form part of an external device in communication (e.g. wirelessly) with the audio processing device. An external device may e.g. comprise another hearing assistance device, a remote control, and audio delivery device, a telephone (e.g. a Smartphone), an external sensor, etc.

In an embodiment, one or more of the number of detectors operate(s) on the full band signal (time domain). In an embodiment, one or more of the number of detectors operate(s) on band split signals ((time-) frequency domain).

In an embodiment, the number of detectors comprises a level detector for estimating a current level of a signal of the forward path. In an embodiment, the predefined criterion comprises whether the current level of a signal of the forward path is above or below a given (L-)threshold value.

In a particular embodiment, the audio processing device comprises a voice detector (VD) for determining whether or not an input signal comprises a voice signal (at a given point in time). A voice signal is in the present context taken to include a speech signal from a human being. It may also include other forms of utterances generated by the human speech system (e.g. singing). In an embodiment, the voice detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only comprising other sound sources (e.g. artificially generated noise). In an embodiment, the voice detector is adapted to detect as a VOICE also the user's own voice. Alternatively, the voice detector is adapted to exclude a user's own voice from the detection of a VOICE.

In an embodiment, the audio processing device comprises an own voice detector for detecting whether a given input sound (e.g. a voice) originates from the voice of the user of the system. In an embodiment, the microphone system of the audio processing device is adapted to be able to differentiate between a user's own voice and another person's voice and possibly from NON-voice sounds.

In an embodiment, the hearing assistance device comprises a classification unit configured to classify the current situation based on input signals from (at least some of) the detectors, and possibly other inputs as well. In the present context 'a current situation' is taken to be defined by one or more of a) the physical environment (e.g. including the current electromagnetic environment, e.g. the occurrence of electromagnetic signals (e.g. comprising audio and/or control signals) intended or not intended for reception by the audio processing device, or other properties of the current environment than acoustic;

b) the current acoustic situation (input level, feedback, etc.), and c) the current mode or state of the user (movement, temperature, etc.);

d) the current mode or state of the hearing assistance device (program selected, time elapsed since last user interaction, etc.) and/or of another device in communication with the audio processing device.

In an embodiment, the audio processing device further comprises other relevant functionality for the application in question, e.g. compression, amplification, feedback reduction, etc.

In an embodiment, the audio processing device comprises a listening device, such as a hearing device, e.g. a hearing aid, e.g. a hearing instrument, e.g. a hearing instrument adapted for being located at the ear or fully or partially in the ear canal of a user, e.g. a headset, an earphone, an ear protection device or a combination thereof.

Use:

In an aspect, use of a audio processing device as described above, in the 'detailed description of embodiments' and in the claims, is moreover provided. In an embodiment, use is provided in a system comprising audio distribution. In an embodiment, use is provided in a system comprising one or more hearing instruments, headsets, ear phones, active ear protection systems, etc., e.g. in handsfree telephone systems, teleconferencing systems, public address systems, karaoke systems, classroom amplification systems, etc.

A method:

In an aspect, a method of estimating an a priori signal to noise ratio (k,n) of a time-frequency representation Y(k,n) of an electric input signal representing a time variant sound signal consisting of target speech components and noise components, where k and n are frequency band and time frame indices, respectively, is furthermore provided by the present application. The method comprises determining an a posteriori signal to noise ratio estimate $\gamma(k,n)$ of said electric input signal Y(k,n);

determining an a priori target signal to noise signal ratio estimate $\zeta(k,n)$ of said electric input signal from said a posteriori signal to noise ratio estimate $\gamma(k,n)$ based on a recursive algorithm;

determining said a priori target signal to noise signal ratio estimate $\zeta(k,n)$ for the $n^{th}$ timeframe from said a priori target signal to noise signal ratio estimate $\zeta(k,n-1)$ for the $(n-1)^{th}$ timeframe and said a posteriori signal to noise ratio estimate $\gamma(k,n)$ for the $n^{th}$ timeframe.

In a further aspect of the present application, a method of estimating an a priori signal to noise ratio $\zeta(k,n)$ of a time-frequency representation Y(k,n) of an electric input signal representing a time variant sound signal consisting of target speech components and noise components, where k and n are frequency band and time frame indices, respectively, is furthermore provided by the present application. The method comprises determining an a posteriori signal to noise ratio estimate $\gamma(k,n)$ of said electric input signal Y(k,n);

determining an a priori target signal to noise signal ratio estimate $\zeta(k,n)$ of said electric input signal from said a posteriori signal to noise ratio estimate $\gamma(k,n)$ based on a recursive algorithm; wherein said recursive algorithm implements a low pass filter with an adaptive time constant or low-pass cut-off frequency.

It is intended that some or all of the structural features of the device described above, in the 'detailed description of embodiments' or in the claims can be combined with embodiments of the method, when appropriately substituted by a corresponding process and vice versa. Embodiments of the method have the same advantages as the corresponding devices.

In an embodiment, the estimates of magnitudes Â(k,n) of said target speech components are determined from said electric input signal Y(k,n) multiplied by a gain function G, where said gain function G is a function of said a posteriori signal to noise ratio estimate $\gamma(k,n)$ and said a priori target signal to noise signal ratio estimate $\zeta(k,n)$.

In an embodiment, the method comprises providing an SNR-dependent smoothing, allowing for more smoothing in low SNR conditions than for high SNR conditions.

In an embodiment, the method comprises a smoothing parameter ($\lambda$) and/or a bias parameter ($\rho$) and/or a bypass parameter $\kappa$.

In an embodiment, the smoothing parameter ($\lambda$) and/or a bias parameter ($\rho$) depend on the a posteriori SNR $\gamma$, or on the spectral density of the electric input signal $|Y|^2$ and the noise spectral density $<\sigma^2>$. In an embodiment, the smoothing parameter ($\lambda$) and/or a bias parameter ($\rho$) and/or the parameter $\kappa$ are selected depending on a user's hearing loss, cognitive skills or speech intelligibility score. In an embodiment, the smoothing parameter ($\lambda$) and/or a bias parameter ($\rho$) and/or the parameter $\kappa$ are selected to provide more smoothing the poorer the hearing ability, cognitive skill or speech intelligibility skills are for the user in question.

In an embodiment, the method comprises adjusting the smoothing parameter ($\lambda$) in order to take a filter bank oversampling into account.

In an embodiment, the method comprises providing that the smoothing and/or the bias parameters depend on whether the input is increasing or decreasing.

In an embodiment, the method comprises providing that the smoothing parameter ($\lambda$) and/or a bias parameter ($\rho$) and/or the parameter $\kappa$ are selectable from a user interface. In an embodiment, the user interface is implemented as an APP of a smartphone.

In an embodiment, the method comprises providing pre-smoothing of the maximum likelihood SNR estimator $\zeta^{ML}(k,n)$ of the a priori target signal to noise ratio estimate $\zeta(k,n)$ for the $n^{th}$ time frame maximum likelihood by a selected minimum value $\xi_{min}^{ML}$. This is used to cope with case $$\frac{|Y_n|^2}{\hat{\sigma}_n^2} < 1.$$

In an embodiment, the recursive algorithm is configured to allow the maximum likelihood SNR estimate to bypass the a priori estimate of the previous frame in the calculation of the bias and smoothing parameters. In an embodiment, the recursive algorithm is configured to allow the current maximum likelihood SNR estimate $s_n^{ML}$ to bypass the a priori estimate $s_{n-1}$ of the previous frame, if the current maximum-likelihood SNR estimate $s_n^{ML}$ minus a parameter $\kappa$ is larger than the previous a priori SNR estimate $s_{n-1}$ (cf. FIG. 4). In an embodiment, the value that is fed to the mapping unit MAP in FIG. 4 is $s_n^{ML}-\kappa$, as shown in FIG. 4, but in another embodiment, $s_n^{ML}$ is directly fed to the mapping unit MAP (when the condition $(s_n^{ML}-\kappa>s_{n-1})$ is fulfilled). In an embodiment, the recursive algorithm comprises a maximum operator (cf. e.g. max in FIG. 4) located in the recursive loop, allowing the maximum likelihood SNR estimate to bypass the a priori estimate of the previous frame in the calculation of the bias and smoothing parameters via a parameter $\kappa$. In an embodiment, the recursive algorithm comprises a selector (cf. e.g. select in FIG. 12A, 12B, 12C) located in the recursive loop, allowing the maximum likelihood SNR estimate to bypass the a priori estimate of the previous frame in the calculation of the bias and smoothing parameters ($92$, $\lambda$) via a parameter $\kappa$. In an embodiment, the selector is controlled by a select control parameter (cf. Onset flag in FIG. 12A, 12B, 12C). In an embodiment, the select control parameter for a given frequency index k (also termed frequency channel k) is determined in dependence of the first, a posteriori, and/or the second, a priori, signal to noise ratio estimates corresponding to a number of frequency indices k', e.g. at least including neighboring frequency indices k−1, k, k+1, e.g. according to a predefined (or adaptive) scheme. In an embodiment, the select control parameter for a given frequency index k is determined in dependence of inputs from one or more detectors (e.g. onset indicators, wind noise or voice detectors, etc.). Thereby (large) SNR onsets can be immediately detected (and thus the risk over-attenuation of speech onsets can be reduced).

In an embodiment, the a posteriori signal to noise ratio estimate $\gamma(k,n)$ of said electric input signal $Y(k,n)$ is provided as a combined a posteriori signal to noise ratio generated as a mixture of a first and a second a posteriori signal to noise ratio. Other combinations (than the a posteriori estimates) can be used (e.g. the noise variance estimate $<\sigma^2>$).

In an embodiment, the two a posteriori signal to noise ratios are generated from a single microphone configuration and from a multi-microphone configuration, respectively. In an embodiment, the first a posteriori signal to noise ratio is generated faster than the second a posteriori signal to noise ratio. In an embodiment, the combined a posteriori signal to noise ratio is generated as a weighted mixture of the first and the second a posteriori signal to noise ratios. In an embodiment, the first and a second a posteriori signal to noise ratios that are combined to the a posteriori signal to noise ratio of an ipsi-lateral hearing aid originate from the ipsi-lateral and a contra-lateral hearing aid, respectively, of a binaural hearing aid system.

A Computer Readable Medium:

In an aspect, a tangible computer-readable medium storing a computer program comprising program code means for causing a data processing system to perform at least some (such as a majority or all) of the steps of the method described above, in the 'detailed description of embodiments' and in the claims, when said computer program is executed on the data processing system is furthermore provided by the present application.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

A Computer Program:

A computer program (product) comprising instructions which, when the program is executed by a computer, cause the computer to carry out (steps of) the method described above, in the 'detailed description of embodiments' and in the claims is furthermore provided by the present application.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

A Hearing System:

In a further aspect, a hearing system comprising an audio processing device as described above, in the 'detailed description of embodiments', and in the claims, AND an auxiliary device is moreover provided.

In an embodiment, the system is adapted to establish a communication link between the audio processing device and the auxiliary device to provide that information (e.g. control and status signals, possibly audio signals) can be exchanged or forwarded from one to the other.

In an embodiment, the audio processing device is or comprises a hearing device, e.g. a hearing aid. In an embodiment, the audio processing device is or comprises a telephone.

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the audio processing device. In an embodiment, the auxiliary device is or comprises a remote control for controlling functionality and operation of the audio processing device or hearing device(s). In an embodiment, the function of a remote control is implemented in a SmartPhone, the SmartPhone possibly running an APP allowing to control the functionality of the audio processing device via the SmartPhone (the audio processing device(s) comprising an appropriate wireless interface to the SmartPhone, e.g. based on Bluetooth or some other standardized or proprietary scheme).

In an embodiment, the auxiliary device is another audio processing device, e.g. a hearing device, such as a hearing aid. In an embodiment, the hearing system comprises two hearing devices adapted to implement a binaural hearing system, e.g. a binaural hearing aid system.

An APP:

In a further aspect, a non-transitory application, termed an APP, is furthermore provided by the present disclosure. The APP comprises executable instructions configured to be executed on an auxiliary device to implement a user interface for a hearing device or a hearing system described above in the 'detailed description of embodiments', and in the claims. In an embodiment, the APP is configured to run on cellular phone, e.g. a smartphone, or on another portable device allowing communication with said hearing device or said hearing system.

Definitions

In the present context, a 'hearing device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing device may comprise a single unit or several units communicating electronically with each other.

More generally, a hearing device comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit for processing the input audio signal and an output means for providing an audible signal to the user in dependence on the processed audio signal. In some hearing devices, an amplifier may constitute the signal processing circuit. The signal processing circuit typically comprises one or more (integrated or separate) memory elements for executing programs and/or for storing parameters used (or potentially used) in the processing and/or for storing information relevant for the function of the hearing device and/or for storing information (e.g. processed information, e.g. provided by the signal processing circuit), e.g. for use in connection with an interface to a user and/or an interface to a programming device. In some hearing devices, the output means may comprise an output transducer, such as e.g. a loudspeaker for providing an air-borne acoustic signal or a vibrator for providing a structure-borne or liquid-borne acoustic signal. In some hearing devices, the output means may comprise one or more output electrodes for providing electric signals.

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A 'hearing system' refers to a system comprising one or two hearing devices, and a 'binaural hearing system' refers to a system comprising two hearing devices and being adapted to cooperatively provide audible signals to both of the user's ears. Hearing systems or binaural hearing systems may further comprise one or more 'auxiliary devices', which communicate with the hearing device(s) and affect and/or benefit from the function of the hearing device(s). Auxiliary devices may be e.g. remote controls, audio gateway devices, mobile phones (e.g. SmartPhones), public-address systems, car audio systems or music players. Hearing devices, hearing systems or binaural hearing systems may e.g. be used for compensating for a hearing-impaired person's loss of hearing capability, augmenting or protecting a normal-hearing person's hearing capability and/or conveying electronic audio signals to a person.

Embodiments of the disclosure may e.g. be useful in applications such as hearing aids, headsets, ear phones, active ear protection systems, handsfree telephone systems, mobile telephones, etc.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

for the STSA gain function, =0.98, and

Figure 6A:
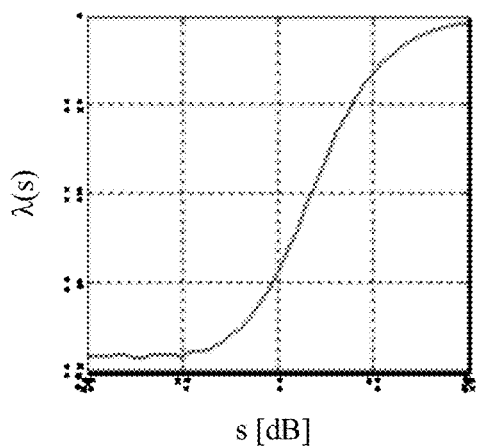
FIG. 6A shows the slope λ of the function $10 \log_{10}$ $$\Psi\left(\xi_{n-1}, \frac{\xi_n^{ML}}{\xi_{n-1}}\right)$$
Figure 6B:
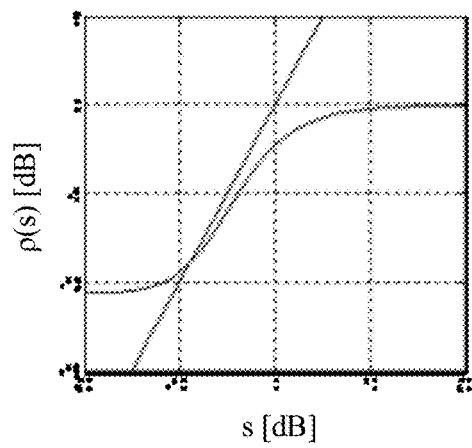
Figure 7:
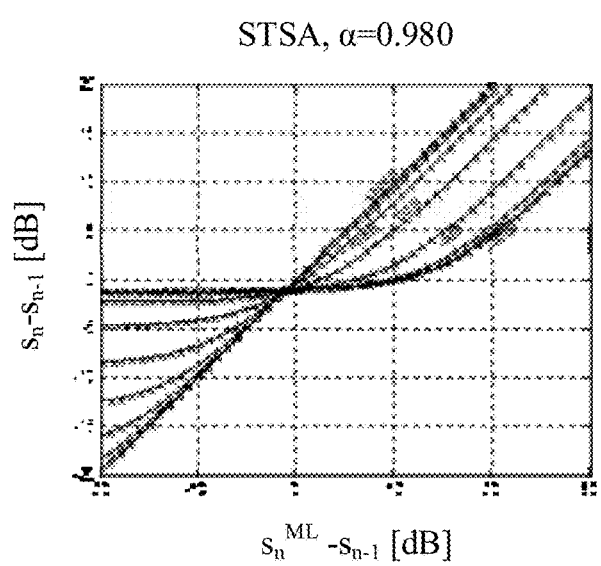
Figure 8:
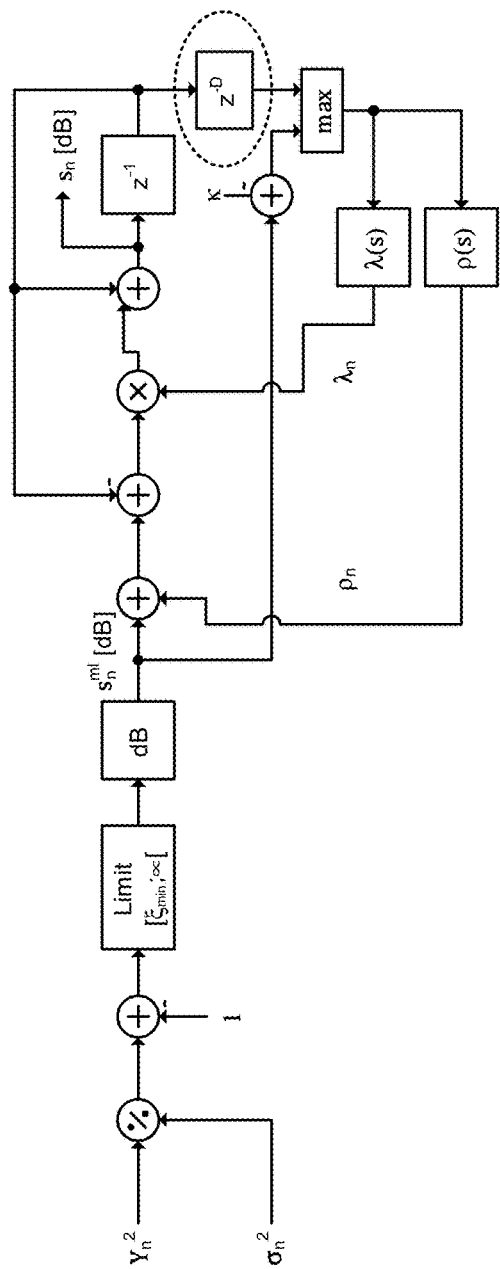
Figure 9A:
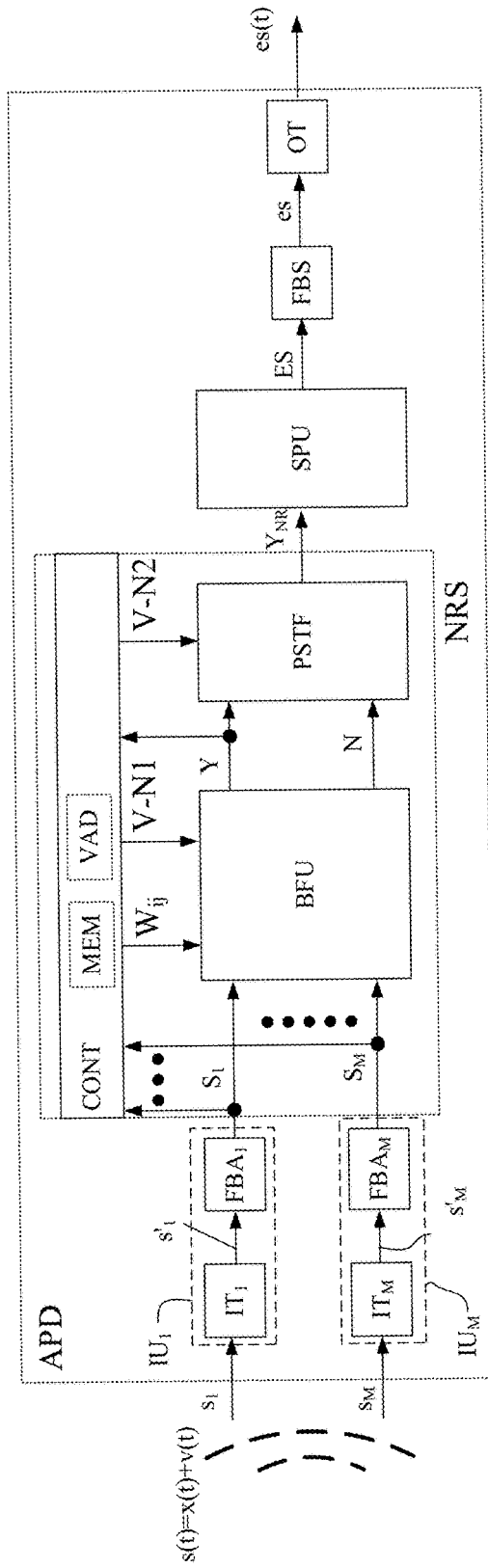
Figure 9B:
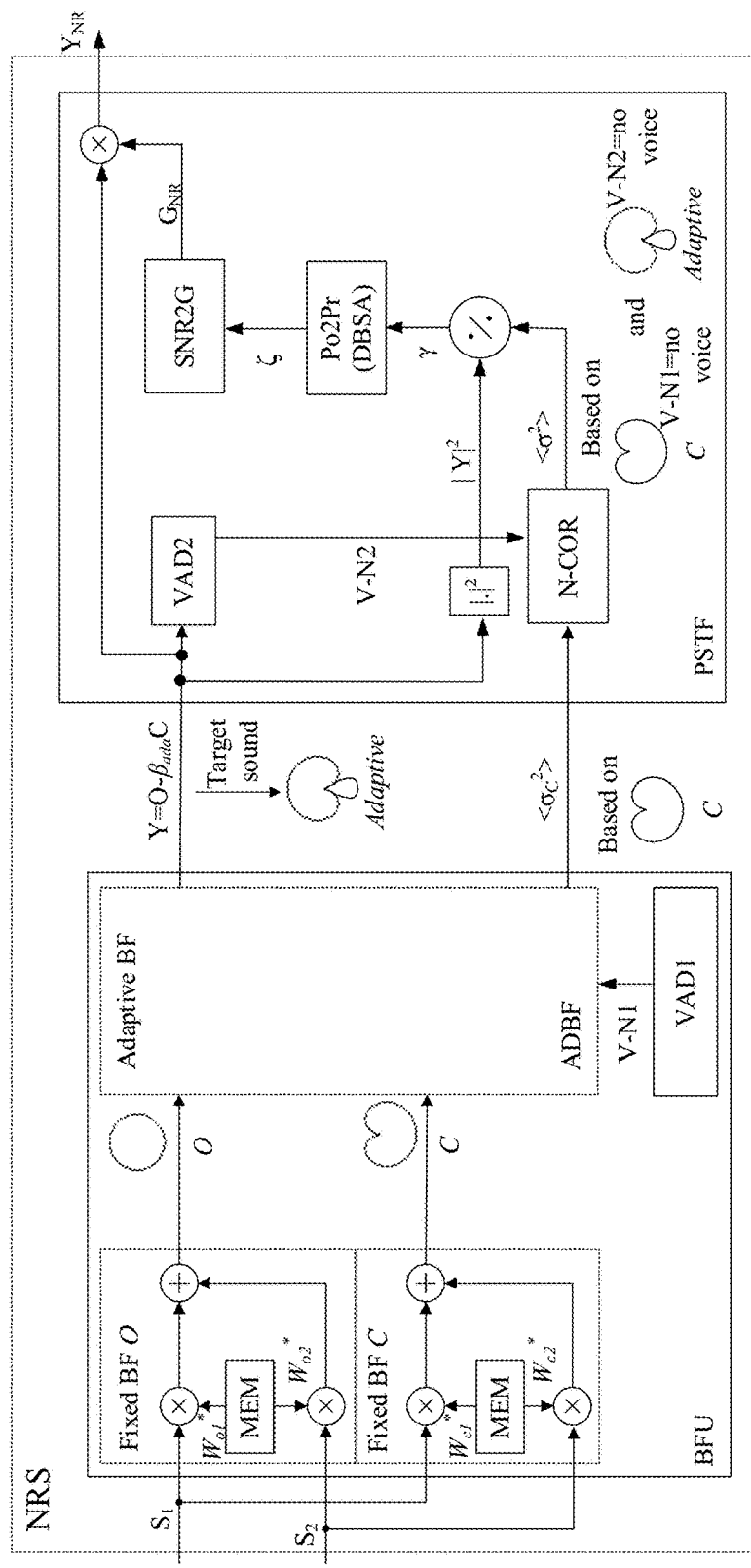
Figure 10:
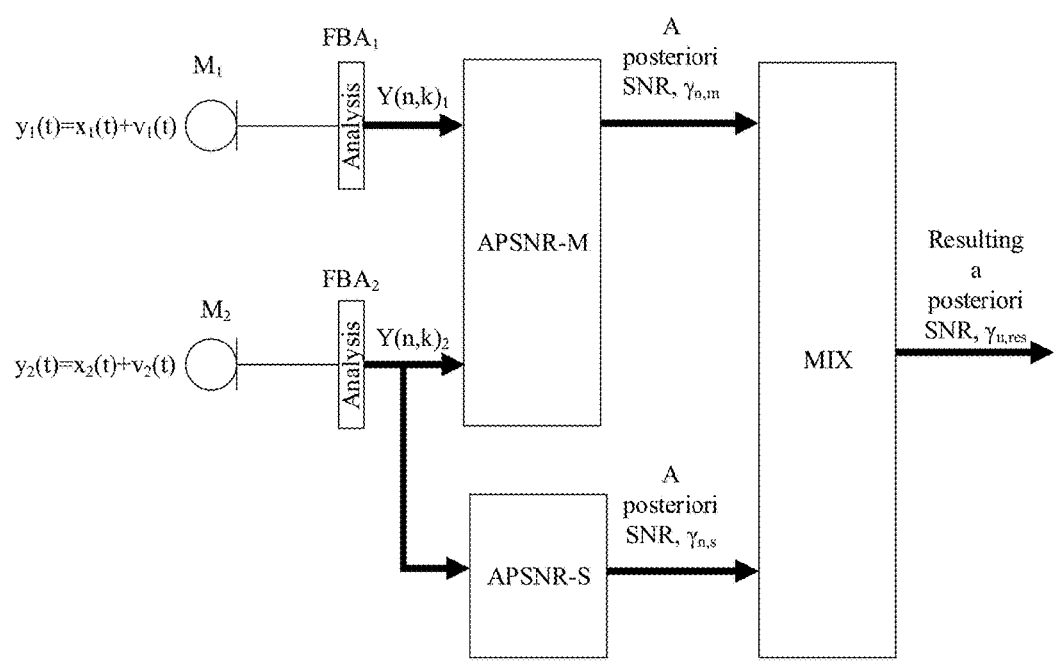
Figure 11:
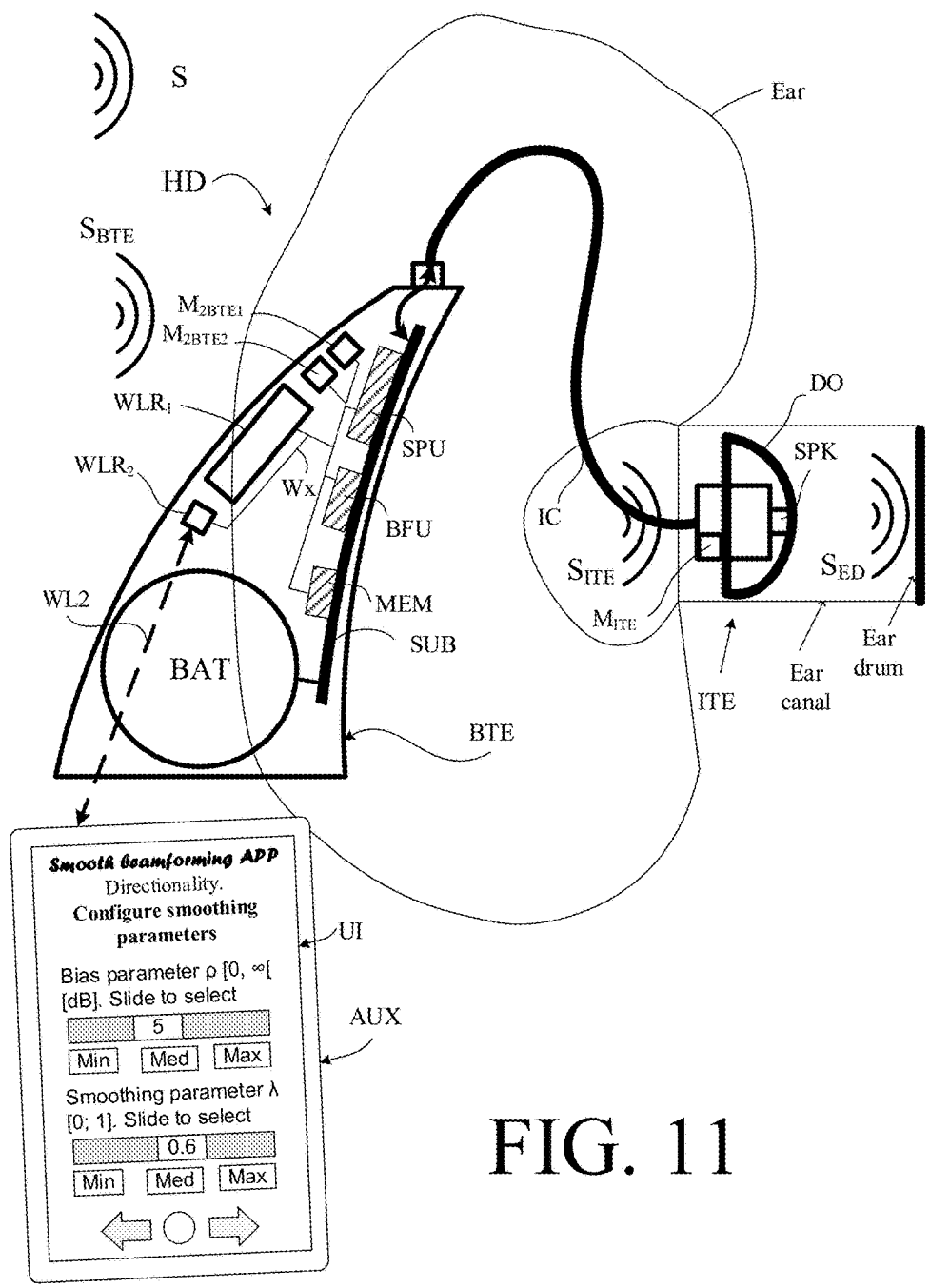
Figure 12A:
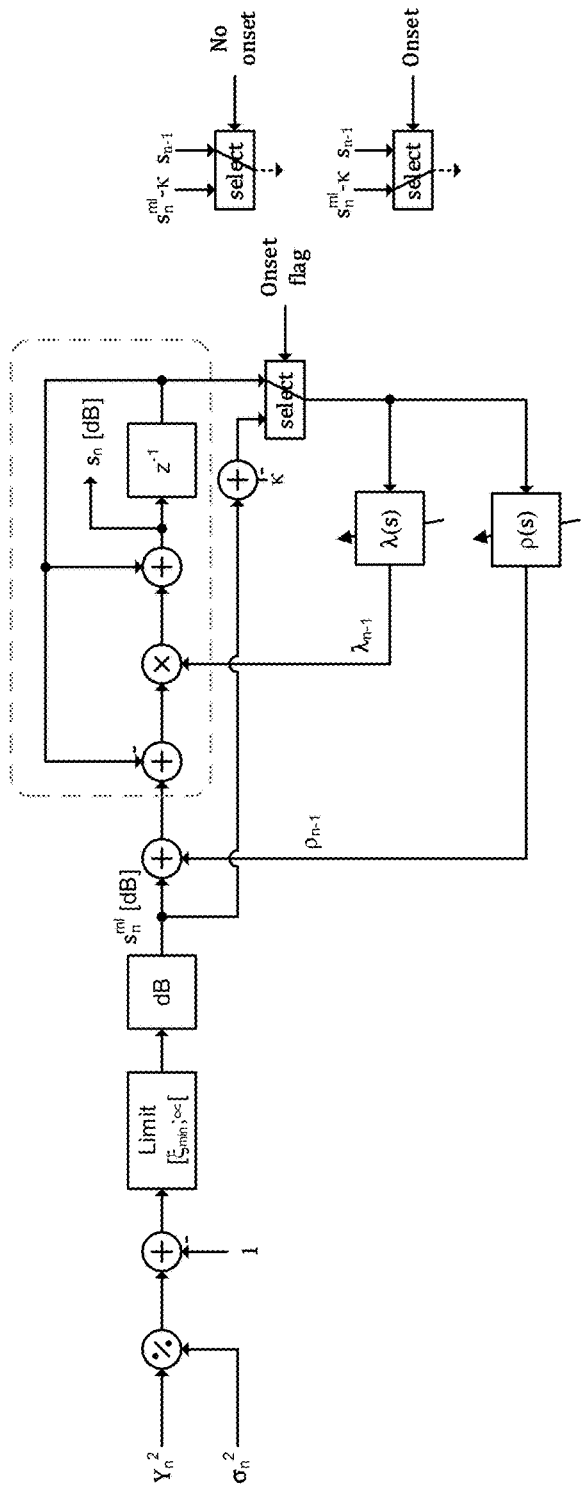
Figure 12B:
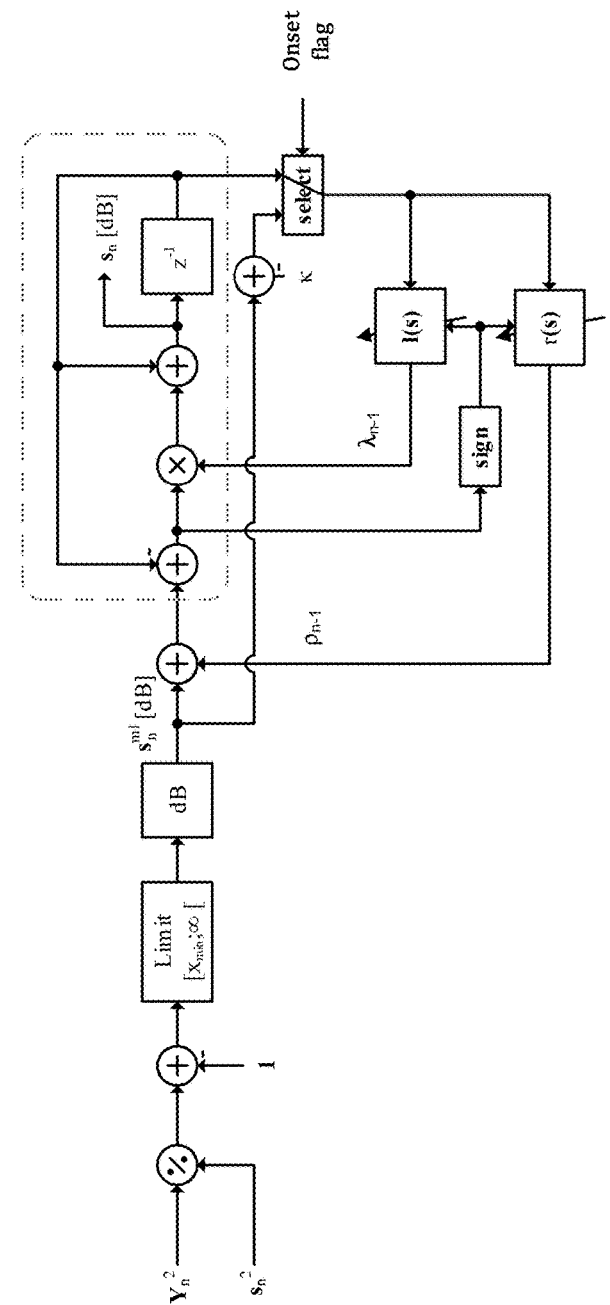
Figure 12C:
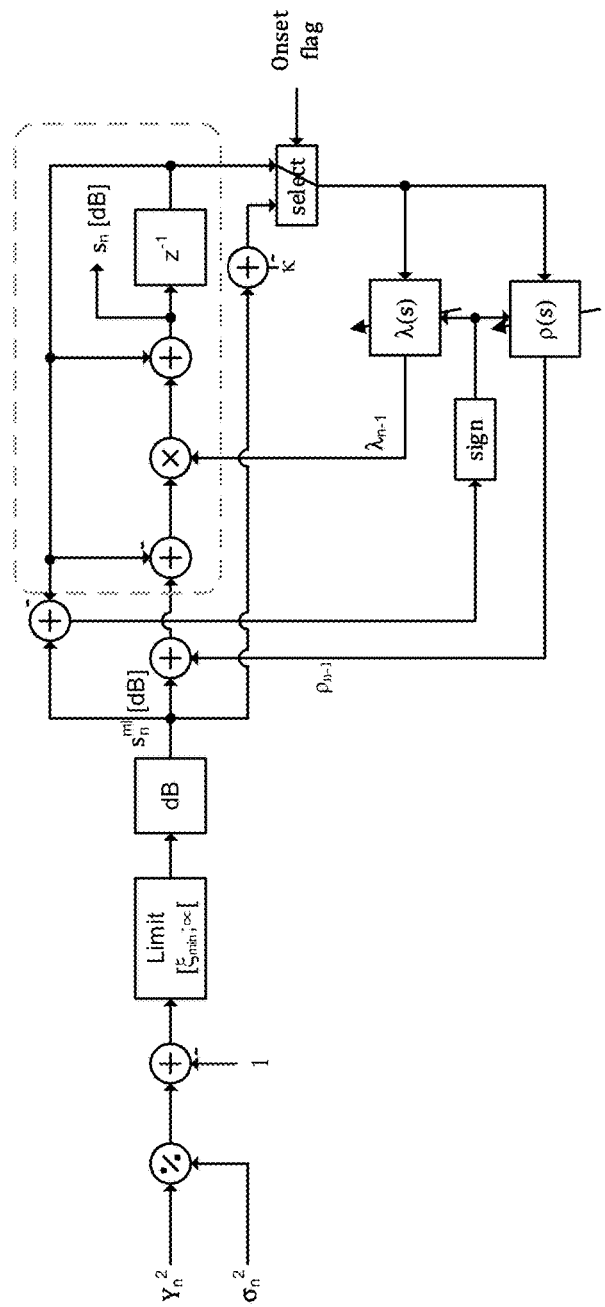
Figure 13A:
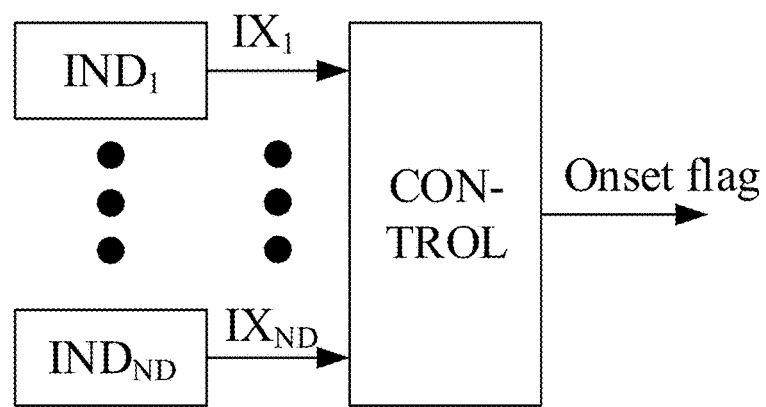

FIG. 6B shows the zero crossing ρ of the function $10 \log_{10}$ $$\Psi\left(\xi_{n-1}, \frac{\xi_n^{ML}}{\xi_{n-1}}\right)$$

for the STSA gain function, =0.98,

FIG. 7 shows a comparison of the responses of the DBSA algorithm according to the present disclosure (crosses) and the DD-algorithm (lines) using the fitted functions in FIG. 6A, 6B, where the curves represent a priori SNR values ranging from −30 dB to +30 dB in 5 dB steps, FIG. 8 illustrates a modification of the DBSA algorithm (shown in FIG. 4) to accommodate filter bank oversampling, where the purpose of inserting an additional D-frame delay in the recursive loop is to mimic the dynamic behavior of a system with less oversampling, FIG. 9A shows an embodiment of an audio processing device, e.g. a hearing aid, according to the present disclosure, and FIG. 9B shows an embodiment of a noise reduction system according to the present disclosure, e.g. for use in the exemplary audio processing device of FIG. 9A (for M=2), FIG. 10 illustrates the generation of a combined a posteriori signal to noise ratio from two a posteriori signal to noise ratios, one being generated from a single microphone channel and the other from a multi-microphone configuration, FIG. 11 shows an embodiment of a hearing aid according to the present disclosure comprising a BTE-part located behind an ear or a user and an ITE part located in an ear canal of the user, FIG. 12A shows a diagram of a first further exemplary implementation of the proposed Directed Bias and Smoothing Algorithm (DBSA, as e.g. implemented by unit Po2Pr in FIG. 1A, 1B), FIG. 12B shows a diagram of a second further exemplary implementation of the proposed Directed Bias and Smoothing Algorithm, and FIG. 12C shows a diagram of a third further exemplary implementation of the proposed Directed Bias and Smoothing Algorithm, and FIG. 13A shows a general example of providing an onset flag for use in the embodiments of the DBSA algorithms illustrated in FIG. 12A, 12B, 12C, and FIG. 13B shows an exemplary embodiment of an onset detector (controller) based on inputs from neighboring frequency bands providing an onset flag for possible use in the embodiments of the DBSA algorithms illustrated in FIG. 12A, 12B, 12C.

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The present application relates to the field of hearing devices, e.g. hearing aids.

Speech enhancement and noise reduction can be obtained by applying a fast-varying gain in the time-frequency domain. The objective of applying the fast-varying gain is to maintain time-frequency tiles dominated by speech unaltered while the time-frequency tiles dominated by noise is suppressed. Hereby, the resulting modulation of the enhanced signal increases, and will typically become similar to the modulation of the original speech signal, leading to a higher speech intelligibility.

Let us assume that the observed signal y(t) is the sum of target speech signal x(t) and noise v(t), (e.g. picked up by a microphone or a number of microphones) processed in an analysis filter bank (FBA; FBA$_1$, FBA$_2$) to yield frequency sub-band signals $Y_{kn}$ (Y(n,k)) corresponding to frequency k (the frequency index k is dropped from here on for simplicity of notation) and time frame n (cf. e.g. FIG. 1A, 1B). For example, $Y_n$ may comprise (or consist of) complex coefficients obtained from a DFT filter bank. Spectral speech enhancement methods rely on estimating the amount of target signal (X) compared to the amount of noise (N) in each time-frequency tile, i.e. the signal-to-noise (SNR) ratio. In spectral noise reduction, SNR is typically described using two different terms: 1) the a posteriori SNR defined as $$\gamma_n = \frac{|Y_n|^2}{\hat{\sigma}_n^2}$$

Where $\hat{\sigma}_n^2$ is an estimate of the noise spectral density (noise spectral power variance) in the $n^{th}$ time frame, and 2) the a priori SNR defined as $$\xi_n = \frac{\langle |X_n|^2 \rangle}{\hat{\sigma}_n^2}.$$

Where $|X_n|^2$ is the target signal spectral density. The a posteriori SNR requires an estimate of the noise power spectral density $\hat{\sigma}_n^2$, while the a priori SNR requires access to both speech $(X_n|^2)$ and noise power $(\hat{\sigma}_n^2)$ spectral densities. If the a priori SNR is available, we can for each unit in time and frequency find an estimate of the target signal as $$\hat{X}_n = \frac{\xi_n}{\xi_n + 1} Y_n,$$

which represents a Wiener gain approach. Other SNR to gain functions may be used, though. The terms 'a posteriori' and 'a priori' signal-to-noise-ratio are e.g. used in [4].

Figure 1A:
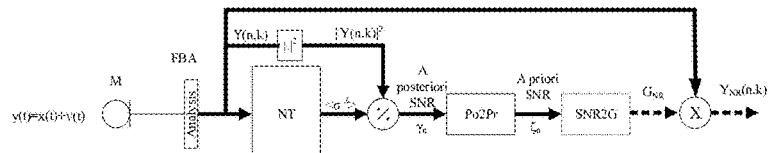
FIG. 1A illustrates a single-channel noise reduction unit, wherein a single microphone (M) obtains a mixture y(t) of target sound (x) and noise (v)
Figure 1B:
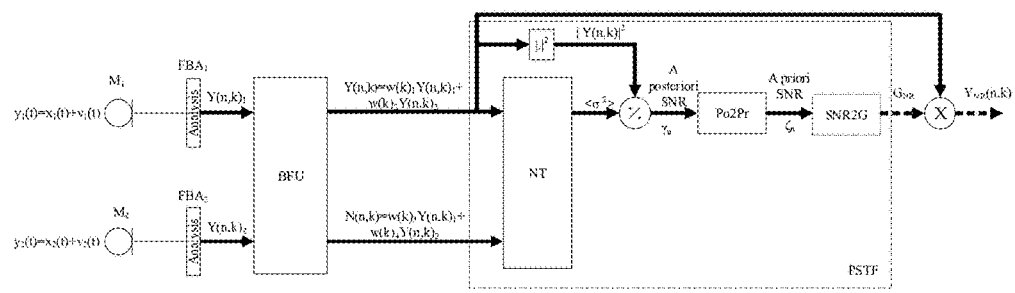
FIG. 1B illustrates a multi-channel noise reduction unit, wherein a multitude of microphone(s) ($M_1$, $M_2$) obtain a mixture y(t) of target sound (x) and noise (v)

FIG. 1A shows a single-channel noise reduction unit, wherein a single microphone (M) receives a mixture y(t) of target sound (x) and noise (v), and FIG. 1B illustrates a multi-channel noise reduction unit, wherein a multitude of microphone(s) ($M_1$, $M_2$) receive a mixture y(t) of target sound (x) and noise (v).

In the present disclosure it is assumed that analogue to digital conversion units are applied as appropriate to provide digitized electric input signals from the microphones. Likewise, it is assumed that digital to analogue conversion unit(s) is/are applied to output signals, if appropriate (e.g. to signals that are to be converted to acoustic signals by a loudspeaker).

The mixture(s) is/are transformed into the frequency domain by respective analysis filter banks (denoted FBA (Analysis) and $FBA_1$ (Analysis), $FBA_2$ (Analysis) in FIGS. 1A and 1B, respectively) and obtaining the signal Y(n,k) (denoted Y(n,k) and $Y(n,k)_1$, $Y(n,k)_2$ in FIGS. 1A and 1B, respectively). In each case, the a posteriori SNR γ(A posteriori SNR, $\gamma_n$ in FIGS. 1A and 1B) is found as the ratio between the power spectral density $|Y_n|^2$ (provided by respective magnitude squared calculation units $|\cdot|^2$) containing the target signal and an estimate of noise power spectral density $\hat{\sigma}_n^2$ (denoted <$\sigma^2$> in FIG. 1A, 1B, and provided by respective noise estimation units NT) within the mixture (cf. combination unit '·/·' in FIG. 1A, 1B). In the case of more than one microphone (e.g. FIG. 1B), the noise within the mixture may be reduced by a linear combination of the microphone signals Y(n,k)=w(k)$_1$·Y(n,k)$_1$+w(k)$_2$·Y(n,k)$_2$, and the remaining noise may be better estimated by using another linear combination (N(n,k)) of the microphone signals aiming at cancelling the target signal, N(n,k)=w(k)$_3$·Y(n,k)$_1$+w(k)$_4$·Y(n,k)$_2$, as indicated by output signals from the beam former filtering unit BFU in FIG. 1B.

The a priori signal to noise ratio (A priori SNR, $\zeta_n$ in FIG. 1A, 1B) is determined by conversion unit Po2Pr implementing an algorithm according to the present disclosure, which is further described in the following. The a priori SNR may e.g. be converted to a gain in an optional SNR to gain conversion unit SNR2G providing a resulting current noise reduction gain $G_{NR}$ (e.g. based on a Wiener gain function), which may be applied to the signal Y(n,k) (input signal in FIG. 1A and spatially filtered signal in FIG. 1B) in combination unit 'X' to provide noise reduced signal $Y_{NR}(n,k)$.

Given that an estimate of the noise power density $\hat{\sigma}_n^2$ (denoted <$\sigma^2$> in FIG. 1A, 1B) is available, we can find the a posteriori SNR directly (cf. combination (here division) unit '·/·' in FIG. 1A, 1B). As we typically do not have access to the target power spectral density ($A_n^2$), $A_n$ being an estimate of the unknown target magnitude $|X_n|$, we do not have direct access to the a priori SNR. In order to estimate the a priori SNR, the decision directed (DD) algorithm has been proposed [1]:

$$\xi_n = \alpha \frac{\hat{A}_{n-1}^2}{\hat{\sigma}_n^2} + (1-\alpha)\max(0, \gamma_n - 1), \quad (1)$$

where $\hat{A}_n$ is the an estimate of the target signal magnitude (in the $n^{th}$ time frame), $\hat{\sigma}_n^2$ is the noise spectral variance (power spectral density) at the frequency in question, and α is a weighting factor. The above expression is a linear combination of two estimates of the a priori SNR $\xi_n$: (because γ−1=(|Y|$^2$/σ$^2$)−1=(|Y|$^2$−σ$^2$)/σ$^2$)~ζ) a recursive part $$\frac{\hat{A}_{n-1}^2}{\hat{\sigma}_n^2}$$

(since $\hat{A}_n$ generally depends on $\xi_n$) and 2) a non-recursive part max(0, $\gamma_n$−1). The weighting parameter α is typically chosen in the interval 0.94-0.99, but obviously α may depend on the frame rate, and possibly other parameters. The noise estimate $\hat{\sigma}_n^2$ is assumed to be available from a spectral noise estimator, e.g. a noise tracker (cf. e.g. [2] EP2701145A1 [3]), e.g. using a voice activity detector and a level estimator (estimating noise levels when no voice is detected; working in frequency sub-bands). The speech magnitude estimate $\hat{A}_n$ is obtained using a speech estimator, of which several are available. Generally, the speech estimator can be represented by the corresponding gain function G $$\hat{A}_n = G(\xi_n, \gamma_n)|Y_n|. \quad (2)$$

The gain function can be chosen depending on a cost function or objective to be minimized, and on the statistical assumptions w.r.t. the speech and noise processes. Well-known examples are the STSA gain function [1], LSA [4], MOSIE [5], Wiener, and spectral subtraction gain functions [5], [7]. While STSA (STSA=minimum-mean square error Short-Time Spectral Amplitude estimator), LSA, and MOSIE depend on both the (estimated) a priori SNR $\xi_n$ and the a posteriori SNR $$\gamma_n = \frac{|Y_n|^2}{\hat{\sigma}_n^2},$$

the Wiener and spectral subtraction gain functions are one-dimensional and depend only on $\xi_n$. As described in [5], $\hat{A}_n$ can be estimated using the following equation known as the MOSIE estimator:

$$\hat{A}_n = \sqrt{\frac{\xi_n}{\mu + \xi_n}} \left[ \frac{\Gamma\left(\mu + \frac{\beta}{2}\right)}{\Gamma(\mu)} \frac{\Phi\left(1 - \mu - \frac{\beta}{2}, 1; -\upsilon_n\right)}{\Phi(1 - \mu, 1; -\upsilon_n)} \right]^{1/\beta} \sqrt{\hat{\sigma}_n^2}, \quad (3)$$

where Γ(.) is the gamma function, Φ(a, b; x) is the confluent hypergeometric function and $$\upsilon_n = \frac{\xi_n}{\mu + \xi_n} \gamma_n.$$

Combining (2) and (3), we can write $$G(\xi_n, \gamma_n) = \sqrt{\frac{\xi_n}{\mu + \xi_n}} \left[ \frac{\Gamma\left(\mu + \frac{\beta}{2}\right)}{\Gamma(\mu)} \frac{\Phi\left(1 - \mu - \frac{\beta}{2}, 1; -\upsilon_n\right)}{\Phi(1 - \mu, 1; -\upsilon_n)} \right]^{1/\beta} \frac{1}{\sqrt{\gamma_n}}.$$

The LSA estimator (cf. e.g. [4]) can be well approached having β=0.001 and μ=1 (cf. e.g. [5]). The a priori SNR estimated by the decision-directed approach is thus a smoothed version of $\max(0, \gamma_n-1)$ depending on the smoothing factor α as well as the chosen estimator for obtaining $\hat{A}_n$.

As mentioned above, α may depend on the frame rate. In an embodiment, the decision directed approach as originally proposed in [1] is designed with frames shifted every $8^{th}$ millisecond (ms). In hearing instruments, the frames are typically updated with a much higher frame rate (e.g. every single millisecond). This higher oversampling factor of the filter bank allows the system to react much faster (e.g. in order to better maintain speech onsets). This advantage of a possible faster reaction time cannot fully be achieved just by adjusting α according to the higher frame rate. Instead we propose a method, which is better at taking advantage of a higher oversampling factor.

The DD-algorithm (1) can be reformulated as the recursive function $$\xi_n = f(\xi_{n-1}, \gamma_{n-1}, \gamma_n) = \qquad (4)$$

$$\alpha G\left(\xi_{n-1}, \frac{|Y_{n-1}|^2}{\hat{\sigma}_{n-1}^2}\right)^2 \frac{|Y_{n-1}|^2}{\hat{\sigma}_n^2} + (1-\alpha)\max\left(0, \frac{|Y_n|^2}{\hat{\sigma}_n^2} - 1\right)$$

As a first simplification, we consider a slightly modified algorithm, which we will refer to as DD*. The recursion in DD* is changed to depend only on the current frame observations and on the previous a priori estimate:

$$\xi_n = F(\xi_{n-1}, \gamma_n) = \alpha G\left(\xi_{n-1}, \frac{|Y_n|^2}{\hat{\sigma}_n^2}\right)^2 \frac{|Y_n|^2}{\hat{\sigma}_n^2} + (1-\alpha)\max\left(0, \frac{|Y_n|^2}{\hat{\sigma}_n^2} - 1\right) \qquad (5)$$

The effect on the a priori estimates by this modification can be quantified by numerical simulations (see later sections), where the effect is found to be generally small, albeit audible. In fact, using the most recent frame power for the a posteriori SNR in the gain function seems beneficial for SNR estimation at speech onsets.

Now, consider the maximum likelihood SNR estimator, which expresses the SNR value with highest likelihood; we make here the standard assumptions that the noise and speech processes are uncorrelated Gaussian processes, and that the spectral coefficients are independent across time and frequency [1]. Then, the maximum likelihood SNR estimator $\xi_n^{ML}$ is given by:

$$\xi_n^{ML} = \max\left(\xi_{min}^{ML}, \frac{|Y_n|^2}{\hat{\sigma}_n^2} - 1\right). \qquad (6)$$

Note that the maximum likelihood estimator is not a central estimator because its mean differs from the true value. In this case an example of a central estimator is $$\frac{|Y_n|^2}{\hat{\sigma}_n^2} - 1,$$

which can take negative values.

Figure 2:
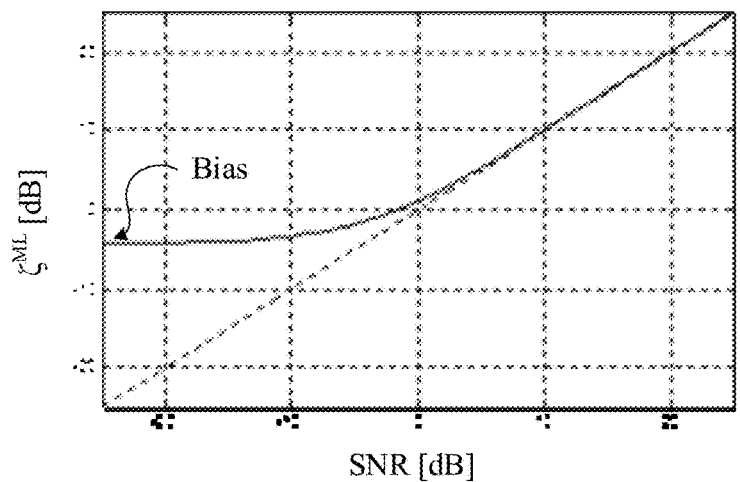
FIG. 2 shows <the mean value of the maximum likelihood estimator $\xi_n^{ML}$ in [dB] as a function of the true SNR in [dB], illustrating the bias, which is introduced by the one-way rectification in the maximum likelihood a priori SNR estimate $\xi_n^{ML}=\max(\xi_{min}^{ML},\gamma_n-1)$.

FIG. 2 shows <the mean value of the maximum likelihood estimator $\xi_n^{ML}$ in [dB] as a function of the true SNR in [dB], illustrating the bias, which is introduced by the one-way rectification in the maximum likelihood a priori SNR estimate $\xi_n^{ML}=\max(\xi_{min}^{ML}, \gamma_n-1)$. The target signal is assumed Gaussian. For noise-only input, the estimated SNR equals $\xi^{ML}=e^{-1}\approx-4.3$ dB (assuming that $\xi_{min}^{ML}=0$, cf. also [5]), cf. Bias in FIG. 2. One effect of the DD approach is to provide a compensation for this bias.

Input-Output Relationship

In the following a functional approximation of the DD* algorithm in Equation (5) is proposed. For mathematical convenience, we assume in the following that $$\frac{|Y_n|^2}{\hat{\sigma}_n^2} \geq 1,$$

and derive such an approximation. This assumption simplifies the non-recursive part because $\xi_n=\max(0, \gamma_n-1)$ simplifies to $\xi_n=\gamma_n-1$ and $\gamma_n=\xi_n+1$. It can be shown that the impact (on results) of this assumption is indeed minor. Thus, ignoring the cases, where $$\frac{|Y_n|^2}{\hat{\sigma}_n^2} < 1,$$

the DD* algorithm in Equation (5) can be described as the following function of $\xi_n^{ML}$ $$\xi_n = \Psi\left(\xi_{n-1}, \frac{\xi_n^{ML}}{\xi_{n-1}}\right)\xi_{n-1}. \qquad (7)$$

As $$\frac{\xi_n}{\xi_{n-1}} = \Psi\left(\xi_{n-1}, \frac{\xi_n^{ML}}{\xi_{n-1}}\right),$$

the function Ψ maps out the relative change in the a priori estimate as function of the ratio between the current $\xi_n^{ML}$ and the previous a priori SNR estimate $\xi_{n-1}$. We thus have $$\Psi\left(\xi_{n-1}, \frac{\xi_n^{ML}}{\xi_{n-1}}\right) = \alpha G(\xi_{n-1}, \xi_n^{ML}+1)^2(\xi_n^{ML}+1) + (1-\alpha)\max(0, \xi_n^{ML}). \qquad (8)$$

By representing the SNR ratios on a logarithmic (dB) scale, the above relationship expresses the non-linear input-output relationship represented by the DD*-algorithm.

Figure 3:
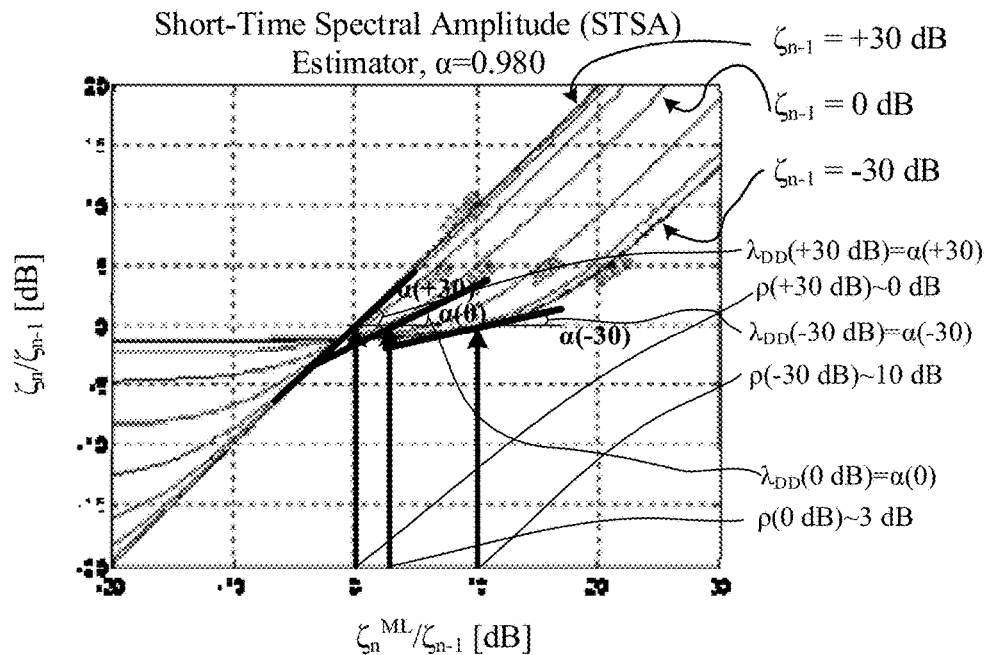
FIG. 3 shows <an input-output relationship ($\Delta_{output}$=f($\Delta_{input}$)) of the DD*-algorithm by numerical evaluation of Equation (7) for the STSA [1] gain function (with α=0.98)

FIG. 3 shows <an input-output relationship (Δoutput=f(Δinput)) of the DD*-algorithm by numerical evaluation of Equation (7) for the STSA [1] gain function (with α=0.98). At low a priori SNR estimates (e.g., curve labeled −30 dB), smoothing is in effect since small changes in output for moderate input changes. Furthermore, a bias is introduced—seen by the non-zero abscissa zero crossings—resulting in the average estimated a priori SNR being lower than the average maximum likelihood SNR estimate. Although the term "bias" is often used to reflect a difference between an expected value E( ) and a "true" reference value, the term is here used to reflect the difference between expected values $E(\xi_n^{ml})$ and $E(\xi_n)$. FIG. 3 gives a graphical relationship allowing the determination of a difference between (or ratio of) the current a priori SNR estimate $\zeta_n$ and the previous a priori SNR estimate $\zeta_{n-1}$ (output) from knowledge of the difference between (or ratio of) the current maximum-likelihood estimates $\xi_n^{ML}$ and the previous a priori SNR estimate $\zeta_{n-1}$ (and the absolute value of the previous a priori SNR estimate $\zeta_{n-1}$) (input).

FIG. 3 shows this relationship, revealing two noticeable effects: For low a priori SNR values (e.g. the curve labelled $\zeta_{n-1}=-30$ dB), the output changes are smaller than the input changes, effectively implementing a low-pass filtering/smoothing of the maximum likelihood SNR estimates $\xi_n^{ML}$. For high a priori SNR values ($\zeta_{n-1}=+30$ dB), the DD* a priori SNR estimate $\xi_n$ varies as much as the change in $\xi_n^{ML}$, resulting in a very small amount of smoothing. Secondly, the zero crossings of the curves for low a priori SNR values are shifted to positive dB values of $$\frac{\xi_n^{ML}}{\xi_{n-1}},$$

up to about 10 dB. This means that for low SNR regions, the a priori SNR estimate $\xi_n$ should settle at values approximately 10 dB below the average value of $\xi^{ML}$.

FIG. 3 gives a graphical relationship allowing the determination of a difference between (or ratio of) the current a priori SNR estimate $\zeta_n$ and the previous a priori SNR estimate $\zeta_{n-1}$ (output) from knowledge of the difference between (or ratio of) the current maximum-likelihood estimate $\xi_n^{ML}$ and the previous a priori SNR estimate $\zeta_{n-1}$ (and the absolute value of the previous a priori SNR estimate $\zeta_{n-1}$) (input).

Values of a smoothing parameter ($\lambda_{DD}$) and a bias parameter ($\rho$) to be discussed below can be read from the graphs as indicated in FIG. 3 for graphs relating to a priory SNR $\zeta_{n-1}=-30$ dB, $\zeta_{n-1}=0$ dB, and $\zeta_{n-1}=+30$ dB. The bias parameter $\rho$ is found as the zero-crossing of the graph with the horizontal axis. The smoothing parameter $\lambda_{DD}$ is found as the slope indicated as $\alpha(\cdot)$ of the graph in question at the zero crossing. These values are e.g. extracted and stored in a table for relevant values of the a priori SNR, cf. e.g. mapping unit MAP in FIG. 4.

Figure 4:
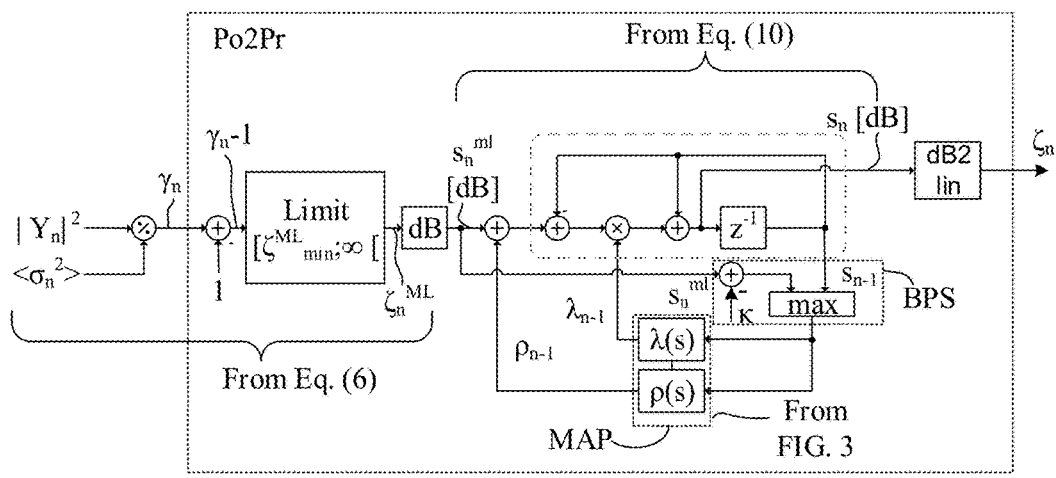
FIG. 4 shows a diagram of an exemplary implementation of the proposed Directed Bias and Smoothing Algorithm (DBSA, implemented by unit Po2Pr)

FIG. 4 shows a diagram of an exemplary implementation of the proposed Directed Bias and Smoothing Algorithm (DBSA) implemented in the conversion unit Po2Pr.

The Directed Bias and Smoothing Algorithm (DBSA)

FIG. 4 shows a diagram of the proposed Directed Bias and Smoothing Algorithm (DBSA, implemented by unit Po2Pr), the aim of which is to provide a configurable alternative implementation of the DD approach, encompassing three main effects of DD 1. An SNR-dependent smoothing, allowing for more smoothing in low SNR conditions reducing musical noise.
2. A negative bias compared to $\xi_n^{ML}$ for low SNR conditions, reducing audibility of musical noise in noise-only periods.
3. A recursive bias, allowing fast switching from low-to-high and high-to-low SNR conditions.

The DBSA algorithm operates with SNR estimates in the dB domain; thus, introduce $$s_n^{ml}=10\log_{10}(\xi_n^{ml}),$$

and $$s_n=10\log_{10}(\xi_n).$$

The central part of the embodiment of the proposed algorithm is a $1^{st}$ order IIR low pass filter with unit DC-gain, and an adaptive time constant. The two functions $\lambda(s_n)$ and $\rho(s_n)$ control the amount of smoothing and the amount of SNR bias, as a recursive function of the estimated SNR.

In the following we will derive the controlling functions so as to mimic the input-output relationship of the DD system described above. Let $s_n$ and $s_n^{ML}$ be the a priori and maximum likelihood SNR expressed in dB, and ignoring the max-operation (let $\kappa \to \infty$ for now) the DBSA input-output relationship is defined by $$s_n - s_{n-1} = (s_n^{ML} + \rho(s_{n-1}) - s_{n-1})\lambda(s_{n-1}) \quad (9)$$

Thus, equating the DBSA to the DD* approach is equivalent to the approximation $$s_n - s_{n-1} = (s_n^{ML} + \rho(s_{n-1}) - s_{n-1})\lambda(s_{n-1}) \quad (10)$$
$$\approx 10\log_{10}\Psi\left(\xi_{n-1}, \frac{\xi_n^{ML}}{\xi_{n-1}}\right)$$

In order to fully specify the DBSA in (10), the bias function $\rho(s_n)$ and the smoothing function $\lambda(s_n)$ must be specified. Since our goal is to mimic the behavior of the DD* approach, we could e.g. measure the zero-crossing location and the slope at this location of the function $$10\log_{10}\Psi\left(\xi_{n-1}, \frac{\xi_n^{ML}}{\xi_{n-1}}\right),$$

(evaluated as a function of $\xi_n^{ML}$), and choose the functions $\rho(s_n)$ and $\lambda(s_n)$ to have the same values. Thus, for the bias function $\rho(s_n)$ we choose it to be equal to the value of $$10\log_{10}\frac{\xi}{\xi_{n-1}}$$

with $\xi$ satisfying $$10\log_{10}\Psi\left(\xi_{n-1}, \frac{\xi}{\xi_{n-1}}\right) = 0 \text{ dB}.$$

Likewise, the smoothing function $\lambda(s_{n-1})$ can be set to equal the slope (w.r.t. $s_n^{ML}$) of the curves in FIG. 3 at the location of its 0 dB crossing (i.e. when $s_n^{ML}-s_n=-\rho(s_{n-1})$).

Figure 5:
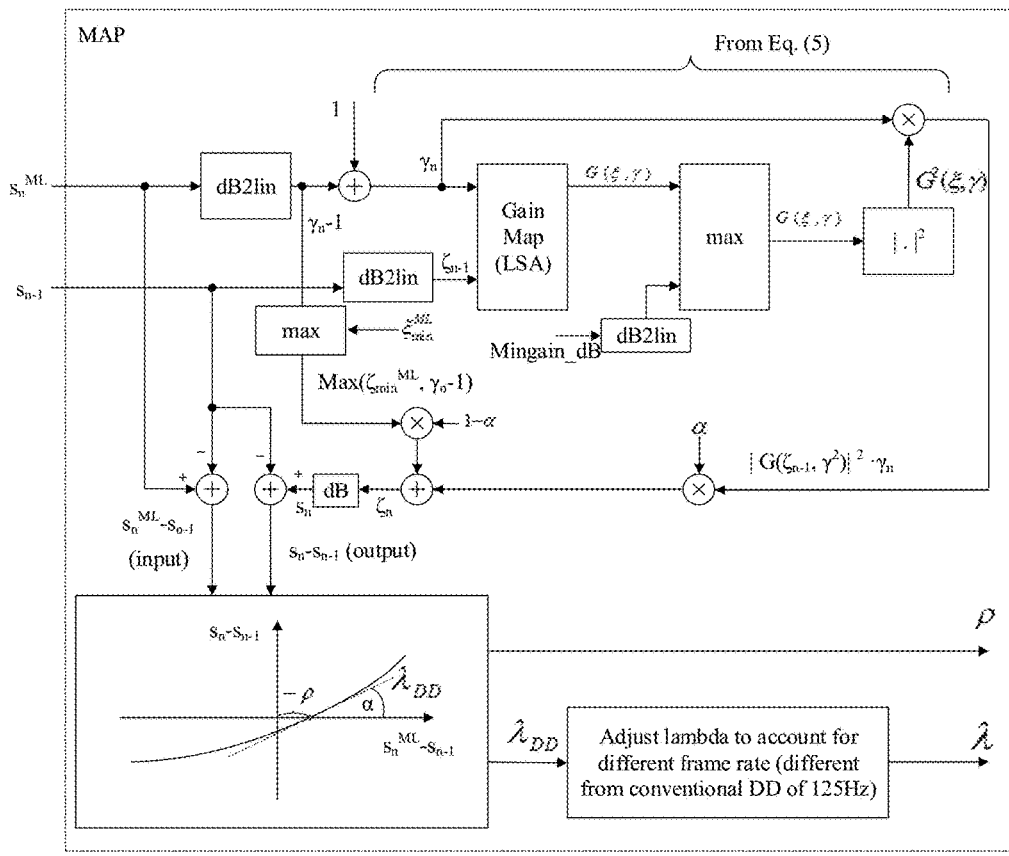
FIG. 5 illustrates how ρ and λ may be derived from the parameters given by the decision directed approach.

FIG. 4 shows an implementation of the Directed Bias and Smoothing Algorithm (DBSA) alternative to the DD-approach. The dashed box in the upper right part of FIG. 4 represents a $1^{st}$ order IIR low-pass filter with unit DC-gain and variable smoothing coefficient $\lambda(\lambda_{n-1}$ in FIG. 4). This part together with combination unit '+' (providing signal $s_n^{ml}-\rho_{n-1}$) and mapping unit MAP (providing smoothing and bias parameters $\lambda$, $\rho$, respectively) providing the inputs to the $1^{st}$ order IIR low-pass filter implements equation 10 below (cf. indication 'From Eq. (10)' in FIG. 4). The two mapping functions $\lambda(s)$ and $\rho(s)$ (cf. mapping unit MAP) control the amount of smoothing ($\lambda$) and bias ($\rho$), respectively, as a recursive function of the estimated a priori SNR ($s_{n-1}$ ($\zeta_{n-1}$) in FIG. 4). The left part of FIG. 4 providing the maximum likelihood value $\zeta_n^{ml}$ of the a priori signal to noise ratio of the $n^{th}$ time frame implements equation (6) above (cf. indication 'From Eq. (6)' in FIG. 4). The maximum likelihood value $\zeta_n^{ml}$ of the a priori signal to noise ratio is converted to the logarithmic domain by the 'dB' unit. The mapping unit MAP is e.g. implemented as a memory comprising a look-up table with values of smoothing and bias parameters λ and ρ extracted from FIG. 3 (or equivalent data material) (cf. indication 'From FIG. 3' in FIG. 4) for relevant values of the a priori SNR ζ(e.g. for a larger range of ζ and/or for a larger number of values, e.g. one curve for every 5 dB, or one for every dB). An implementation of an algorithm for (off-line) calculation of the relevant smoothing and bias parameters λ and ρ for storage in a memory of the mapping unit MAP is illustrated in FIG. 5. The embodiment of FIG. 4 additionally comprises the bypass branch for larger values of the current maximum-likelihood value $s_n^{ml}(\zeta_n^{ml})$ of the a priori SNR, implemented by unit BPS. The bypass unit BPS comprises combination unit '+' and maximum operator unit 'max'. The combination unit '+' takes bypass parameter κ as input. The value of κ is subtracted from the current maximum-likelihood value $s_n^{ml}$ and the resulting value $s_n^{ml} - \kappa$ is fed to the maximum unit max together with the previous value $s_{n-1}$ of the a priori SNR. Thereby relatively large values (larger than $s_{n-1}+\kappa$) of the current maximum-likelihood value $s_n^{ml}$ ($\zeta_n^{ml}$) of the a priori SNR are allowed to have immediate impact on the input to the mapping unit MAP. In an embodiment, the bypass parameter κ is frequency dependent (i.e. e.g. different for different frequency channels k).

FIG. 5 shows how bias parameter ρ and smoothing parameter λ may be derived from the parameters of the decision directed approach (cf. equation 5). FIG. 5 shows an embodiment of an algorithm for generating relevant data to the mapping unit MAP in FIG. 4. The algorithm determines bias parameter ρ and smoothing parameter from the current maximum-likelihood value $s_n^{ml}$ ($\zeta_n^{ml}$) of the a priori SNR, and the previous a priori SNR value $s_{n-1}$. Contrary to having a single mapping of ρ and λ, we may choose to have different sets of ρ and λ depending on whether the input is increasing or decreasing. That corresponds to having different attack and release values for ρ and λ. Such sets of parameters could be derived from different values of α corresponding to different attack and release times (and subsequently stored in the mapping unit MAP). As mentioned later, a compensation of the smoothing parameter to take account of a frame rate (or frame length) different from the one used in the LSA approach [4] is preferably implemented (so that the values of the smoothing parameter λ stored in the mapping unit are directly applicable). This is further discussed below, e.g. in relation to FIG. 8.

FIG. 6A shows the slope λ and FIG. 6B shows the zero crossing p of the function $$10\log_{10}\Psi\left(\xi_{n-1}, \frac{\xi_n^{ML}}{\xi_{n-1}}\right)$$

for the STSA gain function [1], using α=0.98 in both cases. FIG. 7 shows a comparison of the responses of the DBSA algorithm according to the present disclosure (crosses) and the DD-algorithm (lines) using the fitted functions in FIGS. 6A and 6B, where the curves represent a priori SNR values ranging from −30 dB to +30 dB in 5 dB steps.

FIG. 6 shows the results from numerical evaluation, and FIG. 7 shows a comparison between the input-output responses of the DD*-algorithm and the DBSA algorithm.

The difference is seen to be quite small in most cases, as shown in the simulations in a later section.

The Case of Low Observed SNR

Now, consider the case $$\frac{|Y_n|^2}{\hat{\sigma}_n^2} < 1.$$

In DBSA, this case is caught by the minimum value $\xi_{min}^{ML}$, which limits the influence. Recalling Equation (2), $$\hat{A}_n = G\left(\xi_n, \frac{|Y_n|^2}{\hat{\sigma}_n^2}\right)|Y_n|,$$

we note that the class of gain functions that can be expressed as a power of the Wiener gain function generally have that $\hat{A}_n \to 0$ when $$\frac{|Y_n|^2}{\hat{\sigma}_n^2} \to 0.$$

This property makes the DD-algorithm bias quite large and negative, which can be mimicked in DBSA with a relatively low value of $\xi_{min}^{ML}$.

On the other hand, for the STSA, LSA and MOSIE gain functions, a gain larger than 0 dB occurs when $$\frac{|Y_n|^2}{\hat{\sigma}_n^2} \to 0$$

resulting in a non-zero $\hat{A}_n$ in the limit. This effect can to some extent by handled by a larger $\xi_{min}^{ML}$. In practice the remaining difference between the DD* approach and DBSA can be made to be negligible.

Numerical Issues

It should be noted that in some cases (typically for low a priori SNR values) the function $$10\log_{10}\Psi\left(\xi_{n-1}, \frac{\xi_n^{ML}}{\xi_{n-1}}\right)$$

does not have a zero crossing. This reflects a limitation in the range of actual a priori SNR values that the system can produce. One particular example occurs when the gain function $$G\left(\xi_n, \frac{|Y_n|^2}{\hat{\sigma}_n^2}\right)$$

is limited by some minimum gain value $G_{min}$. Inserting this minimum value into Equation (5) it can easily be shown that $$\Psi\left(\xi_{n-1}, \frac{\xi_n^{ML}}{\xi_{n-1}}\right) \geq \frac{\alpha G_{min}}{\xi_{n-1}}.$$

So when $\xi_{n-1}$ is sufficiently low, the function $\Psi$ will be greater than 1, which again means no zero crossing for the function $10 \log_{10} \Psi$. A numerical implementation will need to detect this situation and specify some reasonable lookup table values for $\rho(s_n)$ and $\lambda(s_n)$ all the same. The exact values used will not matter in reality since they most likely will only be sampled during convergence from an initial state.

The Maximum Operator and More

In FIG. 4, a maximum operator is located in the recursive loop, allowing the maximum likelihood SNR estimate to bypass the a priori estimate of the previous frame in the calculation of the bias and smoothing parameters (via parameter $\kappa$). The reason for this element is to aid the detection of SNR onsets and thus reducing the risk overattenuation of speech onsets. In the DD approach Equation (1), the term $(1-\alpha)$ allows for large onsets in the current frame to reduce the negative bias quickly, the maximum mimics this behavior as controlled by the parameter $\kappa$. We thus have the ability to bypass the smoothing using the factor $\kappa$. By increasing $\kappa$ we may better maintain the speech onsets. On the other hand, an increased $\kappa$ may also raise the noise floor. An increased noised noise floor will however only have influence when we apply a high amount of attenuation. Thus the selected value of $\kappa$ depends on the chosen maximum attenuation.

Instead of the Maximum operator ('max' in FIGS. 4, 5 and 8), a more general selection scheme may be used to identify (sudden) SNR-changes (e.g. onsets), cf. e.g. 'select' unit in the embodiments illustrated in FIGS. 12A, 12B and 12C. Such more general schemes may e.g. include consideration of events (changes) in the acoustic environment (e.g. sudden appearance or removal of noise sources (e.g. wind noise), or sudden changes in other acoustic sources such as speech sources, e.g. own voice), cf. e.g. FIG. 13A and/or include consideration of changes in the signal over a number of frequency bands around the frequency bands considered (e.g. evaluating all frequency bands and applying a logic criterion to provide a resulting onset flag for the frequency band in question), cf. e.g. FIG. 13B.

Filter Bank Oversampling

The filter bank parameters have a large influence on the result of the DD approach. Oversampling is the major parameter to consider, since it has a direct effect on the effect of the smoothing and amount of bias introduced into the a priori SNR estimate.

How to correct for filter bank oversampling in the DD approach has not been well described in the literature. In the original formulation [1], a 256-point FFT was used with a Hanning window, with 192 samples overlap corresponding to four-fold oversampling, and a sample rate of 8 kHz. In general, two-fold oversampling (50% frame overlap) is usual, see [1] and the references therein. In hearing aids and other low-latency applications, however, oversampling by a factor of 16 or higher is not unrealistic.

All things equal, oversampling reduces the recursive effects of the DD-approach, as well as of the DBSA method. In the limit of "infinite" oversampling, the recursive bias is replaced with the asymptotic bias function.

One possible approach for oversampling compensation is to downsample the DD/DBSA estimation by a factor proportional to the oversampling, keeping the priori estimate constant over a number of frames. A drawback of this approach may be that gain jumps are introduced, which may reduce sound quality when used in combination with an oversampled filter bank. With oversampling, the equivalent synthesis filters are shorter and may be insufficient for attenuation of the convolutive noise introduced by the gain jumps.

With the DBSA method, the temporal behavior (i.e. smoothing of SNR estimates and responsiveness to onsets) is controlled by the combination of the directed recursive smoothing, the directed recursive bias. A more computationally demanding but in theory more precise way of handling filter bank oversampling is by means of a higher order delay element (circular buffer) in the recursive loop, as shown in FIG. 8.

FIG. 8 illustrates a modification of the DBSA algorithm (shown in FIG. 4) to accommodate filter bank oversampling, where the purpose of inserting an additional D-frame delay in the recursive loop is to mimic the dynamic behavior of a system with less oversampling. Compared to the embodiment of the DBSA algorithm exemplified in FIGS. 4, 5 and 8, the embodiments illustrated in FIGS. 12A, 12B and 12C are different in that the max operator has been substituted by a select operator (select), which can e.g. be controlled by an onset flag (Onset flag). Contrary to the max operator, which only influences the local frequency channel k, an onset flag may depend on a number of 'control inputs' qualified according to a, e.g. predefined or adaptive (e.g. logic), scheme (cf. e.g. FIG. 1A), and/or including other frequency channels as well (cf. e.g. FIG. 13B). In an embodiment, the bypass parameter $\kappa$ is frequency dependent (i.e. e.g. different for different frequency channels k).

FIG. 12A shows a diagram of a first further exemplary implementation of the proposed Directed Bias and Smoothing Algorithm (DBSA, e.g. as implemented by unit Po2Pr in FIGS. 1A, 1B, and 9B). Contrary to the max operator, which only influences the local frequency channel k, an onset flag may depend on other frequency channels as well (cf. e.g. FIG. 13B). The advantage of an onset flag is (assuming that onsets affects many frequency channels simultaneously) that the onset information which is detected in the few frequency channels having high SNR may be propagated to the frequency channels having a lower SNR. Hereby onset information may be applied faster in the low-SNR frequency channels. In an embodiment, a broad band onset detector can be used as well as the onset flag for a given frequency channel k (or as an input to a criterion for determining the onset flag). Alternatively, if e.g. the bias corrected latest (maximum likelihood ('a priori') estimate of the) SNR value $s_n^{ML}-\kappa$ in a number of the K frequency channels (e.g. the channel in question k and the neighboring channels on each side (e.g. k−1, k+1, cf. FIG. 13B) is higher than the previous ('a priori') SNR value $s_{n-1}$, it is an indication of an onset. Other frequency channels than the immediately neighboring channels and/or other onset indications may be considered in the determination of the onset flag for a given frequency channel k. In an embodiment, the onset flag in a particular frequency channel k is determined in dependence on whether local onsets have been detected in at least q channels, where q is a number between 1 and K.

FIG. 12B shows a diagram of a second further exemplary implementation of the proposed Directed Bias and Smoothing Algorithm (DBSA, e.g. as implemented by unit Po2Pr in FIGS. 1A, 1B, and 9B). In addition to being dependent on the SNR, $\lambda$ and $\rho$ may also depend on whether the SNR is increasing or decreasing. If the SNR increases, as indicated by $s_n^{ML}+\rho_{n-1}-s_{n-1}>0$, we choose one set of $\lambda(s)$ and $\rho(s)$, $\lambda_{atk}(s)$, $\rho_{atk}(s)$, and if the SNR is decreasing, as indicated by $s_n^{ML}+\rho_{n-1}-s_{n-1}<0$, we choose another set of $\lambda(s)$ and $\rho(s)$, $\lambda_{rel}(s)$, $\rho_{rel}(s)$. Exemplary courses of smoothing parameters $\lambda(s)$ and $\rho(s)$ are shown in FIGS. 6A and 6B, respectively.

Furthermore, in another preferred embodiment, the "select" unit may not only depend on a detected onset. It may as well depend on a detected own voice or wind noise or any combination of the mentioned (or other) detectors (cf. e.g. FIG. 13A).

FIG. 12C shows a diagram of a third further exemplary implementation of the proposed Directed Bias and Smoothing Algorithm (DBSA, e.g. as implemented by unit Po2Pr in FIGS. 1A, 1B, and 9B). In addition to being dependent on the SNR, $\lambda$ and $\rho$ may also depend on another indication that the SNR is increasing or decreasing. If the SNR increases, as indicated by $s_n^{ML}-s_{n-1}>0$, we choose one set of $\lambda$ and $\rho$, $\lambda_{atk}$, $\rho_{atk}$, and if the SNR is decreasing, as indicated by $s_n^{ML}-s_{n-1}<0$, we choose another set of $\lambda$ and $\rho$, $\lambda_{rel}$, $\rho_{rel}$.

FIG. 13A shows a general example of providing an onset flag for use in the embodiments of the DBSA algorithms illustrated in FIG. 12A, 12B, 12C. The audio processing device, e.g. a hearing aid, may comprise a number ND of detectors or indicators ($IND_1$, ..., $IND_{ND}$) providing a number of indicators (signals $IX_1$, ..., $IX_{ND}$) of an onset of a change of the acoustic scene around the audio processing device, which may lead to a change of the SNR of the signal considered by a forward path of the audio processing device. Such indicators may e.g. include a general onset detector for detecting sudden changes in the time variant input sound s(t) (cf. e.g. FIG. 9A), e.g. its modulation, a wind noise detector, a voice detector, e.g. an own voice detector, head movement detector, wireless transmission detector, voice detectors from microphones in other audio devices (e.g. other hearing instrument, or external microphones in e.g. smartphones), etc., and combinations thereof. The outputs ($IX_1$, ..., $IX_{ND}$) from the indicators ($IND_1$, ..., $IND_{ND}$) are fed to the controller (CONTROL), which implement an algorithm for providing a resulting onset indicator (signal Onset flag) for a given frequency channel $\underline{k}$. A specific implementation (or partial implementation) of such scheme is illustrated in FIG. 13B.

Figure 13B:
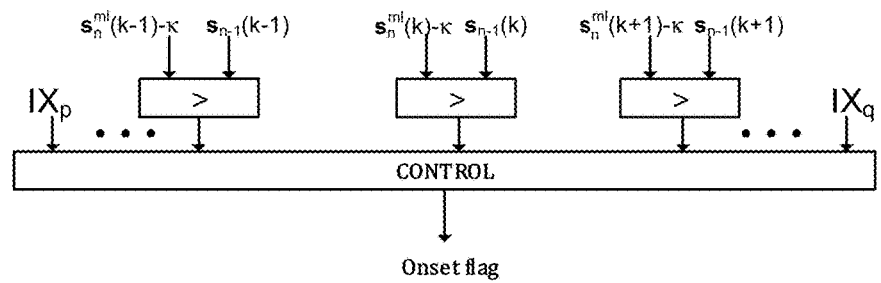

FIG. 13B shows an exemplary embodiment of controller (CONTROL) based on inputs from neighboring frequency bands providing an onset flag for possible use in the embodiments of the DBSA algorithms illustrated in FIG. 12A, 12B, 12C. The illustrated scheme provides input indicator signals ($IX_p$, ..., $IX_q$) including indicators evaluating changes over time of the SNR as indicated by whether $s_n^{ML}(k')-\kappa>s_{n-1}(k')$ is fulfilled over a number of frequency bands k' around the frequency band k considered (e.g. evaluating the expression for k'=k−1, k, and k+1), or for just one of them, or 'two of three', etc., or evaluating the expression for all frequency bands k=1, ..., K, (or a selected range, e.g. where speech and/or noise is expected to occur) and applying a logic criterion to provide a resulting onset flag for the frequency band in question). In an embodiment, only the immediately neighbouring bands to a given channel k are considered, i.e. three channels are included in providing the Onset flag for each channel. In an embodiment, such scheme is combined with inputs from other detectors as mentioned in connection with FIG. 13A. In an embodiment, the expression $s_n^{ML}(k')-\kappa>s_{n-1}(k')$ or other similar expressions, are evaluated for a number of frequency channels around the channel in question, e.g. all channels, and a scheme for providing a resulting Onset flag is applied to the input indicators ($IX_p$, ..., $IX_q$). The bias constant $\kappa$ may be constant over frequency, or different from channel to channel, or different for some channels.

Advantages of the Proposed Implementation

The proposed implementation has the following advantages over the decision directed approach:

We can adjust the smoothing parameter in order to take the filter bank oversampling into account, which is important for implementation in low-latency applications such as hearing instruments.

Rather than having the smoothing and bias depending on the selected gain function, the smoothing $\lambda(s)$ and bias $\rho(s)$ is directly controlled by the parameterization of the two mapping functions. This enables tuning of each of the mapping functions separately for a desired tradeoff between noise reduction and sound quality. E.g. target energy may be better maintained by over-emphasizing the bias. Also, the parameters can be set in order to address a certain range of SNR which is of interest. Such sets of parameters may be chosen different for individual users, as some users mainly benefit from noise reduction (in terms of a fluctuating gain) in low-SNR regions and do not need noise reduction as higher signal to noise ratios. On the other hand, other users may require noise reduction at a higher signal to noise ratio region, and a constant attenuation at low signal to noise ratios.

As an extension to the proposed system, the smoothing and bias parameters may depend on whether the input is increasing or decreasing. I.e. we may use different attack and release values of the two parameters.

The change of the decision directed approach to only depend on the current frame observations and on the previous a priori estimate seems beneficial for the SNR estimation at speech onsets.

Likewise, the maximum operator controlled by the parameter $\kappa$ can be used to reduce the risk of over-attenuating speech onsets. The selected value may depend on the chosen maximum attenuation Pre-smoothing of the $\xi_n^{ML}$ by a selected minimum value $\xi_{min}^{ML}$ is used to cope with case $$\frac{|Y_n|^2}{\hat{\sigma}_n^2} < 1$$

The noise estimator may rely on multichannel as well as single channel inputs, or on both, and/or on binaural inputs, cf. e.g. FIG. 10. The DBSA parameters may be adjusted differently depending on whether the noise estimator relies on a single channel input or multi-channel inputs.

FIG. 9A shows an embodiment of an audio processing device APD, e.g. a hearing aid, according to the present disclosure. A time variant input sound s(t) is assumed to comprise a mixture of a target signal component x(t) and a noise signal component v(t) is picked up by the audio processing device processed and provided in a processed for to a user as an audible signal. The audio processing device—here a hearing aid—of FIG. 9A comprises a multitude of input units $IU_j$, j=1, ..., M, each providing an electric input signal $S_i$ representative of sound s(t) in a time-frequency representation (k,n). In the embodiment of FIG. 9A, each input unit $IU_i$ comprises an input transducer $IT_i$ for converting input sound $s_i$ from the environment (as received at input unit $IU_i$) to an electric time-domain signal $s'_i$, i=1, ..., M. The input unit $IU_i$ further comprises an analysis filter bank $FBA_i$ for converting the electric time-domain signal $s'_i$ to a number of frequency sub-band signals (k=1, ..., K), thereby providing the electric inputs signal in a time-frequency representation $S_i(k,n)$. The hearing aid further comprises a multi-input noise reduction system NRS, providing a noise reduced signal $Y_{NR}$ based on the multitude of electric input signals $S_i$, i=1, . . . , M. The multi-input noise reduction system NRS comprises a multi-input beam former filtering unit BFU, a post filter unit PSTF, and a control unit CONT. The multi-input beam former filtering unit BFU (and the control unit CONT) receives the multitude of electric input signals $S_i$, i=1, . . . , M, and provides signals Y and N. The control unit CONT comprises a memory MEM wherein complex weights $W_{ij}$ are stored. The complex weights $W_{ij}$ define possible pre-defined fixed beam formers of the beam former filtering unit BFU (fed to BFU via signal $W_{ij}$), cf. e.g. FIG. 9B. The control unit CONT further comprises one or more voice activity detectors VAD for estimating whether or not a given input signal (e.g. a given time-frequency unit of the input signal) comprises (or is dominated by) a voice. Respective control signals V-N1 and VN-2 are fed to the beam former filtering unit BFU and to the post filtering unit PSTF, respectively. The control unit CONT receives the multitude of electric input signals $S_i$, i=1, M, from input units and the signal Y from the beam former filtering unit BFU. The signal Y comprises an estimate of the target signal component, and the signal N comprises an estimate of the noise signal component. The (single channel) post filtering unit PSTF receives (spatially filtered) target signal estimate Y and (spatially filtered) noise signal estimate N, and provides a (further) noise reduced target signal estimate $Y_{NR}$ based on knowledge of the noise extracted from the noise signal estimate N. The hearing aid further comprises a signal processing unit SPU for (further) processing the noise reduced signal and providing a processed signal ES. The signal processing unit SPU may be configured to apply a level and frequency dependent shaping of the noise reduced signal $Y_{NR}$, e.g. to compensate for a user's hearing impairment. The hearing aid further comprises a synthesis filter bank FBS for converting the processed frequency sub-band signal ES to a time domain signal es, which is fed to an output unit OT for providing stimuli es(t) to a user as a signal perceivable as sound. In the embodiment of FIG. 9A, the output unit comprises a loudspeaker for presenting the processed signal es to the user as sound. The forward path from the input unit to the output unit of the hearing aid is here operated in the time-frequency domain (processed in a number of frequency sub-bands $FB_k$, k=1, . . . , K). In another embodiment, the forward path from the input unit to the output unit of the hearing aid may be operated in the time domain. The hearing aid may further comprise a user interface and one or more detectors allowing user inputs and detector inputs to be received by the noise reduction system NRS, e.g. the beam former filtering unit BFU. An adaptive functionality of the beam former filtering unit BFU may be provided.

FIG. 9B shows a block diagram of an embodiment of a noise reduction system NRS, e.g. for use in the exemplary audio processing device of FIG. 9A (for M=2), e.g. a hearing aid, according to the present disclosure. An exemplary embodiment of the noise reduction system of FIG. 9A is further detailed out in FIG. 9B. FIG. 9B shows an embodiment of an adaptive beam former filtering unit (BFU) according to the present disclosure. The beam former filtering unit comprises first (omni-directional) and second (target cancelling) beam formers (denoted Fixed BF O and Fixed BF C in FIG. 9B and symbolized by corresponding beam patterns). The first and second fixed beam formers provide beam formed signals O and C, respectively, as linear combinations of first and second electric input signals $S_1$ and $S_2$, where first and second sets of complex weighting constants $(W_{o1}(k)^*, W_{o2}(k)^*)$ and $(W_{c1}(k)^*, W_{c2}(k)^*)$ representative of the respective beam patterns are stored in memory unit (MEM) (cf. memory unit MEM in control unit CONT of FIG. 9A and signal $W_{ij}$). * indicates complex conjugation. The beam former filtering unit (BFU) further comprises an adaptive beam former (Adaptive BF, ADBF) providing adaptation constant $\beta_{ada}(k)$ representative of an adaptively determined beam pattern. By combining the fixed and adaptive beam formers of the beam former filtering unit BFU, a resulting (adaptive) estimate of the target signal Y is provided as $Y=O-\beta_{ada}C$. The beam former filtering unit (BFU) further comprises voice activity detector VAD1 providing control signal V-N1 (e.g. based on signal O or one of the input signals $S_i$) indicative of whether or not (or with what probability) the input signal (here O or one of $S_i$) comprises voice content (e.g. speech) that allows the adaptive beam former to update a noise estimate $<\sigma_c^2>$ (here based on the target cancelling beam former C) during time segments where no (or a low probability of) voice/speech is indicated by the voice activity detector VAD1.

The resulting (spatially filtered or beam formed) target signal estimate Y from the beam former filtering unit can thus be expressed as $$Y(k)=O(k)-\beta_{ada}(k)\cdot C(k)$$

$$Y(k)=(W_{o1}^*\cdot S_1+W_{o2}^*\cdot S_2)-\beta_{ada}(k)\cdot (W_{c1}^*\cdot S_1+W_{c2}^*\cdot S_2)$$

It may, however, be computationally advantageous just to calculate the actual resulting weights applied to each microphone signal rather than calculating the different beam formers used to achieve the resulting signal.

The embodiment of a post filtering unit PSTF in FIG. 9B receives input signals Y (spatially filtered target signal estimate) and $<\sigma_c^2>$ (noise power spectrum estimate) and provides output signal $Y_{BF}$ (noise reduced target signal estimate) based thereon. The post filtering unit PSTF comprises noise reduction correction unit N-COR for improving the noise power spectrum estimate $<\sigma_c^2>$ received from the beam former filtering unit and providing an improved noise power spectrum estimate $<\sigma^2>$. The improvement results from the use of voice activity detector VAD2 to indicate the presence of no-voice time-frequency units in the spatially filtered target signal estimate Y (cf. signal V-N2). The post filtering unit PSTF further comprises magnitude square $(|\cdot|^2)$ and divide $(\cdot/\cdot)$ processing units for providing the target signal power spectrum estimate $|Y|^2$ and a posteriori signal to noise ratio $\gamma=|Y|^2/<\sigma^2>$ respectively. The post filtering unit PSTF further comprises a conversion unit Po2Pr for converting the a posteriori signal to noise ratio estimate $\gamma$ to an a priori signal to noise ratio estimate $\zeta$ implementing an algorithm according to the present disclosure. The post filtering unit PSTF further comprises a conversion unit SNR2G configured to convert the a priori signal to noise ratio estimate $\zeta$ to a corresponding gain $G_{NR}$ to be applied to the spatially filtered target signal estimate (here by multiplication unit 'X') to provide the resulting noise reduced target signal estimate $Y_{BF}$. Frequency and time indices k and n are not shown in FIG. 9B for simplicity. But it is assumed that corresponding time frames are available for the processed signals, e.g. $|Y_n|^2$, $<\sigma_n^2>$, $\gamma_n$, $\zeta_n$, $G_{NR,n}$, etc.).

The multi-input noise reduction system comprising a multi-input beam former filtering unit BFU and a single channel post filtering unit PSTF may e.g. be implemented as discussed in [2] with the modifications proposed in the present disclosure.

The noise power spectrum $<\sigma^2>$ is in the embodiment of FIG. 9B based on the two microphone beam former (the target cancelling beam former C), but may instead be based on a single-channel noise estimate, e.g. based on an analysis of modulation (e.g. a voice activity detector).

FIG. 10 illustrates an input stage (e.g. of a hearing aid) comprising microphones $M_1$ and $M_2$ electrically connected to respective analysis filter banks $FBA_1$ and $FBA_2$ and providing respective mixed electric input frequency sub-band signals $Y(n,k)_1$, $Y(n,k)_2$, as described in connection with FIG. 1B. The electric input signals $Y(n,k)_1$, $Y(n,k)_2$, based on the first and second microphone signals, are fed to a multi-input (here 2) a posteriori signal to noise calculation unit (APSNR-M) for providing multi-input a posteriori SNR $\gamma_{n,m}$ (for the $n^{th}$ time frame), e.g. as discussed in connection with FIG. 1B above. One of the two electric input signals $Y(n,k)_1$, $Y(n,k)_2$, or a third different electric input signal (e.g. beamformed signal or a signal based on a third microphone, e.g. a microphone of a contra-lateral hearing aid or of a separate microphone) is fed to a single-input a posteriori signal to noise calculation unit (APSNR-S) for providing single-input a posteriori SNR $\gamma_{n,s}$ (for the $n^{th}$ time frame), e.g. as discussed in connection with FIG. 1A above. The two a posteriori SNRs $\gamma_{n,m}$ and $\gamma_{n,s}$ are fed to mixing unit MIX for generation of a combined (resulting) a posteriori signal to noise ratio $\gamma_{n,res}$ from the two a posteriori signal to noise ratios. The combination of two independent a posteriori estimates will typically provide a better estimate than each of the estimates alone. As the multichannel estimate $\gamma_{n,m}$ typically is more reliable than the single channel estimate $\gamma_{n,s}$, the multichannel estimate will require less smoothing compared to the single input channel noise estimate. Thus, different sets of the smoothing parameters $\rho$ (bias), $\lambda$ (smoothing), and $\kappa$ (bias) (cf. FIG. 3, 4) are required for smoothing of the multi microphone a posteriori SNR estimate $\gamma_{n,m}$ and the single microphone a posteriori SNR estimate $\gamma_{n,s}$. The mixing of the two estimates to provide the resulting a posteriori SNR estimate $\gamma_{n,res}$ could e.g. be provide as a weighted sum of the two estimates $\gamma_{n,m}$, $\gamma_{n,s}$.

In an embodiment of a binaural hearing aid system, either the a posteriori SNR, the a priori SNR, or the noise estimate or the gain from the hearing instrument on the contralateral side is transmitted to and used in the hearing instrument on the ips-ilateral side.

Besides the a posteriori estimate from the ipsi-lateral hearing instrument, the a priori estimate may also depend on the a posteriori estimate, the a priori, or the noise estimate (or gain estimate) from the contra-lateral hearing instrument. Again, an improved a priori SNR estimate can be achieved by combining different independent SNR estimates.

FIG. 11 shows an embodiment of a hearing aid according to the present disclosure comprising a BTE-part located behind an ear or a user and an ITE part located in an ear canal of the user.

FIG. 11 illustrates an exemplary hearing aid (HD) formed as a receiver in the ear (RITE) type hearing aid comprising a BTE-part (BTE) adapted for being located behind pinna and a part (ITE) comprising an output transducer (e.g. a loudspeaker/receiver, SPK) adapted for being located in an ear canal (Ear canal) of the user (e.g. exemplifying a hearing aid (HD) as shown in FIG. 9A). The BTE-part (BTE) and the ITE-part (ITE) are connected (e.g. electrically connected) by a connecting element (IC). In the embodiment of a hearing aid of FIG. 11, the BTE part (BTE) comprises two input transducers (here microphones) ($M_{BTE1}$, $M_{BTE2}$) each for providing an electric input audio signal representative of an input sound signal ($S_{BTE}$) from the environment (in the scenario of FIG. 11, from sound source S). The hearing aid of FIG. 11 further comprises two wireless receivers (WLR$_1$, WLR$_2$) for providing respective directly received auxiliary audio and/or information signals. The hearing aid (HD) further comprises a substrate (SUB) whereon a number of electronic components are mounted, functionally partitioned according to the application in question (analogue, digital, passive components, etc.), but including a configurable signal processing unit (SPU), a beam former filtering unit (BFU), and a memory unit (MEM) coupled to each other and to input and output units via electrical conductors Wx. The mentioned functional units (as well as other components) may be partitioned in circuits and components according to the application in question (e.g. with a view to size, power consumption, analogue vs digital processing, etc.), e.g. integrated in one or more integrated circuits, or as a combination of one or more integrated circuits and one or more separate electronic components (e.g. inductor, capacitor, etc.). The configurable signal processing unit (SPU) provides an enhanced audio signal (cf. signal ES in FIG. 9A), which is intended to be presented to a user. In the embodiment of a hearing aid device in FIG. 11, the ITE part (ITE) comprises an output unit in the form of a loudspeaker (receiver) (SPK) for converting the electric signal (es in FIG. 9A) to an acoustic signal (providing, or contributing to, acoustic signal $S_{ED}$ at the ear drum (Ear drum). In an embodiment, the ITE-part further comprises an input unit comprising an input transducer (e.g. a microphone) ($M_{ITE}$) for providing an electric input audio signal representative of an input sound signal $S_{ITE}$ from the environment at or in the ear canal. In another embodiment, the hearing aid may comprise only the BTE-microphones ($M_{BTE1}$, $M_{BTE2}$). In yet another embodiment, the hearing aid may comprise an input unit ($IT_3$) located elsewhere than at the ear canal in combination with one or more input units located in the BTE-part and/or the ITE-part. The ITE-part further comprises a guiding element, e.g. a dome, (DO) for guiding and positioning the ITE-part in the ear canal of the user.

The hearing aid (HD) exemplified in FIG. 11 is a portable device and further comprises a battery (BAT) for energizing electronic components of the BTE- and ITE-parts.

The hearing aid (HD) comprises a directional microphone system (beam former filtering unit (BFU)) adapted to enhance a target acoustic source among a multitude of acoustic sources in the local environment of the user wearing the hearing aid device. In an embodiment, the directional system is adapted to detect (such as adaptively detect) from which direction a particular part of the microphone signal (e.g. a target part and/or a noise part) originates and/or to receive inputs from a user interface (e.g. a remote control or a smartphone) regarding the present target direction. The memory unit (MEM) comprises predefined (or adaptively determined) complex, frequency dependent constants defining predefined or fixed (or adaptively determined 'fixed') beam patterns according to the present disclosure, together defining the beamformed signal Y (cf. e.g. FIG. 9A, 9B).

The hearing aid of FIG. 11 may constitute or form part of a hearing aid and/or a binaural hearing aid system according to the present disclosure.

The hearing aid (HD) according to the present disclosure may comprise a user interface UI, e.g. as shown in FIG. 11 implemented in an auxiliary device (AUX), e.g. a remote control, e.g. implemented as an APP in a smartphone or other portable (or stationary) electronic device. In the embodiment of FIG. 11, the screen of the user interface (UI) illustrates a Smooth beamforming APP. Parameters that govern or influence the current smoothing of signal to noise ratios of a beamforming noise reduction system, here parameters $\rho$ (bias), $\lambda$ (smoothing), (cf. discussion in connection with FIG. 3, 4) can be controlled via the Smooth beamforming APP (with the subtitle: 'Directionality. Configure smoothing parameters'). The bias parameter ρ can be set via a slider to a value between a minimum value (e.g. 0) and a maximum value, e.g. 10 dB. The currently set value (here 5 dB) is shown on the screen at the location of the slider on the (grey shaded) bar that span the configurable range of values. Likewise, the smoothing parameter λ can be set via a slider to a value between a minimum value (e.g. 0) and a maximum value, e.g. 1. The currently set value (here 0.6) is shown on the screen at the location of the slider on the (grey shaded) bar that span the configurable range of values. The arrows at the bottom of the screen allow changes to a preceding and a proceeding screen of the APP, and a tab on the circular dot between the two arrows brings up a menu that allows the selection of other APPs or features of the device. The parameters ρ and λ related to smoothing may not necessarily be visible to the user. The sets of ρ, λ could be derived from a third parameter (e.g. a calm to aggressive noise reduction bar or set via an environment detector).

The auxiliary device and the hearing aid are adapted to allow communication of data representative of the currently selected smoothing parameters to the hearing aid via a, e.g. wireless, communication link (cf. dashed arrow WL2 in FIG. 11). The communication link WL2 may e.g. be based on far field communication, e.g. Bluetooth or Bluetooth Low Energy (or similar technology), implemented by appropriate antenna and transceiver circuitry in the hearing aid (HD) and the auxiliary device (AUX), indicated by transceiver unit $WLR_2$ in the hearing aid. The communication link may be configured to provide one-way (e.g. APP to hearing instrument) or two way communication (e.g. audio and/or control or information signals).

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

[1] Ephraim, Y.; Malah, D., "Speech enhancement using a minimum-mean square error short-time spectral amplitude estimator", IEEE Transactions on Acoustics, Speech and Signal Processing, vol. 32, no. 6, pp. 1109-1121, December 1984 URL: http://ieeexplore.ieee.org/stamp/stamp.jsp?tp=&arnumber=1164453&isnumber=26187
[2] EP2701145A1
[3] Martin, R., "Noise Power Spectral Density Estimation Based on Optimal Smoothing and Minimum Statistics", IEEE Transactions on Speech and Audio Processing, vol. 9, no. 5, pp. 504-512, April 2001
[4] Ephraim, Y.; Malah, D., "Speech enhancement using a minimum mean-square error log-spectral amplitude estimator", IEEE Transactions on Acoustics, Speech and Signal Processing, vol. 33, no. 2, pp. 443-445, April 1985 URL: http://ieeexplore.ieee.org/stamp/stamp.jsp?tp=&arnumber=1164550&isnumber=26190
[5] Breithaupt, C.; Martin, R., "Analysis of the Decision-Directed SNR Estimator for Speech Enhancement With Respect to Low-SNR and Transient Conditions", IEEE Transactions on Audio, Speech, and Language Processing, vol. 19, no. 2, pp. 277-289, February 2011 URL: http://ieeexplore.ieee.org/stamp/stamp.jsp?tp=&arnumber=5444986&isnumber=56092 32
[6] Cappe, O., "Elimination of the musical noise phenomenon with the Ephraim and Malah noise suppressor," Speech and Audio Processing, IEEE Transactions on, vol. 2, no. 2, pp. 345-349, April 1994 URL: http://ieeexplore.ieee.org/stamp/stamp.jsp?tp=&arnumber=279283&isnumber=6926
[7] Loizou, P. (2007). Speech Enhancement: Theory and Practice, CRC Press, Boca Raton: Fla.

The invention claimed is:

1. An audio processing device, comprising
at least one input unit for providing a time-frequency representation Y(k,n) of an electric input signal representing a time variant sound signal consisting of target speech signal components S(k,n) from a target sound source TS and noise signal components N(k,n) from other sources than the target sound source, where k and n are frequency band and time frame indices, respectively,
a noise reduction system configured to
determine an a posteriori signal to noise ratio estimate γ(k,n) of said electric input signal,
determine an a priori target signal to noise ratio estimate ζ(k,n) of said electric input signal from said a posteriori signal to noise ratio estimate γ(k,n) based on a recursive algorithm,
determine said a priori target signal to noise ratio estimate ζ(k,n) for the $n^{th}$ timeframe from said a priori target signal to noise ratio estimate ζ(k,n−1)

for the $(n-1)^{th}$ timeframe, and from said a posteriori signal to noise ratio estimate $\gamma(k,n)$ for the $n^{th}$ timeframe, provide a noise reduction gain $G_{NR}$ in dependence of said a priori target signal to noise ratio estimate $\zeta(k,n)$, and apply said noise reduction gain $G_{NR}$ to said electric input signal or a signal derived therefrom, wherein said recursive algorithm is configured to implement a low pass filter with an adaptive time constant or cut-off frequency.

2. An audio processing device according to claim 1 wherein said noise reduction system is configured to determine said a priori target signal to noise ratio estimate $\zeta$ by non-linear smoothing of said a posteriori signal to noise ratio estimate $\gamma$, or a parameter derived therefrom, wherein said non-linear smoothing is controlled by one or more bias and smoothing parameters.

3. An audio processing device according to claim 1 wherein said noise reduction system is configured to determine said a priori target signal to noise ratio estimate $\zeta(k,n)$ for the $n^{th}$ time frame under the assumption that $\gamma(k,n)$ is larger than or equal to 1.

4. An audio processing device according to claim 1 wherein said noise reduction system is configured to determine said a priori target signal to noise ratio estimate $\zeta(k,n)$ for the $n^{th}$ timeframe from said a priori target signal to noise ratio estimate $\zeta(k,n-1)$ for the $(n-1)^{th}$ timeframe, and from a maximum likelihood SNR estimator $\zeta^{ML}(k,n)$ of the a priori target signal to noise ratio estimate $\zeta(k,n)$ for the $n^{th}$ timeframe.

5. An audio processing device according to claim 4 wherein said noise reduction system is configured to determine said maximum likelihood SNR estimator $\zeta^{ML}(k,n)$ as $MAX\{\zeta^{ML}_{min}(k,n); \gamma(k,n)-1\}$, where MAX is the maximum operator, and $\zeta^{ML}_{min}(k,n)$ is a minimum value of the maximum likelihood SNR estimator $\zeta^{ML}(k,n)$.

6. An audio processing device according to claim 4 wherein said noise reduction system is configured to determine said a priori target signal to noise ratio estimate $\zeta(k,n)$ for the $n^{th}$ timeframe from said a priori target signal to noise ratio estimate $\zeta(k,n-1)$ for the $(n-1)^{th}$ timeframe, and from the maximum likelihood SNR estimator $\zeta^{ML}(k,n)$ of the a priori target signal to noise ratio estimate $\zeta(k,n)$ for the $n^{th}$ time frame according to the following recursive algorithm:

$$s_n - s_{n-1} = (s_n^{ML} + \rho(s_{n-1}) - s_{n-1})\lambda(s_{n-1})$$

where $\rho(s_{n-1})$ represents a bias function or parameter and $\lambda(s_{n-1})$ represents a smoothing function or parameter of the $(n-1)^{th}$ time frame.

7. An audio processing device according to claim 4 wherein said noise reduction system is configured to determine said a priori target signal to noise ratio estimate $\zeta$ by non-linear smoothing of said a posteriori signal to noise ratio estimate $\gamma$, or a parameter derived therefrom, wherein said non-linear smoothing is controlled by one or more bias and smoothing parameters, wherein the noise reduction system implements a recursive algorithm that comprises a selector located in the recursive loop, allowing the maximum likelihood SNR estimator of the present time frame n to bypass the a priori estimate of the previous time frame n-1 in the calculation of said bias and smoothing parameters.

8. An audio processing device according to claim 7 wherein the selector is controlled by a select control parameter wherein the select control parameter for a given frequency index k is determined in dependence of the first, a posteriori, and/or the second, a priori, signal to noise ratio estimates corresponding to a number of frequency indices k', at least including neighboring frequency indices k−1, k, k+1, according to a predefined or adaptive scheme.

9. An audio processing device according to claim 7 wherein the select control parameter for a given frequency index k is determined in dependence of inputs from one or more detectors.

10. An audio processing device according to claim 1 wherein said noise reduction system is configured to provide an SNR-dependent smoothing, allowing for more smoothing in low SNR conditions than for high SNR conditions.

11. An audio processing device according to claim 1 wherein said noise reduction system is configured to provide a negative bias compared to $\xi_n^{ML}$ for low SNR conditions.

12. An audio processing device according to claim 11 wherein said noise reduction system is configured to provide a recursive bias, allowing a configurable change from low-to-high and high-to-low SNR conditions.

13. An audio processing device according to claim 1 comprising a filter bank comprising an analysis filter bank for providing said time-frequency representation $Y(k,n)$ of said electric input signal.

14. An audio processing device according to claim 13 configured to provide that said analysis filter bank is oversampled.

15. An audio processing device according to claim 14 wherein the recursive loop of the algorithm for determining said a priori target signal to noise ratio estimate $\zeta(k,n)$ for the $n^{th}$ timeframe comprises a higher order delay element, e.g. a circular buffer.

16. An audio processing device according to claim 14 wherein noise reduction system is configured to adapt the algorithm for determining said a priori target signal to noise ratio estimate $\zeta(k,n)$ for the $n^{th}$ timeframe to compensate for oversampling of the analysis filter bank.

17. An audio processing device according to claim 1 comprising a hearing device.

18. A method of estimating an a priori signal to noise ratio $\zeta(k,n)$ of a time-frequency representation $Y(k,n)$ of an electric input signal representing a time variant sound signal consisting of target speech components and noise components, where k and n are frequency band and time frame indices, respectively, the method comprising determining an a posteriori signal to noise ratio estimate $\gamma(k,n)$ of said electric input signal $Y(k,n)$;

determining an a priori target signal to noise signal ratio estimate $\zeta(k,n)$ of said electric input signal from said a posteriori signal to noise ratio estimate $\gamma(k,n)$ based on a recursive algorithm;

determining said a priori target signal to noise signal ratio estimate $\zeta(k,n)$ for the $n^{th}$ timeframe from said a priori target signal to noise signal ratio estimate $\zeta(k,n-1)$ for the $(n-1)^{th}$ timeframe and said a posteriori signal to noise ratio estimate $\gamma(k,n)$ for the $n^{th}$ timeframe;

providing a noise reduction gain $G_{NR}$ in dependence of said a priori target signal to noise ratio estimate $\zeta(k,n)$; and applying said noise reduction gain $G_{NR}$ to said electric input signal or a signal derived therefrom, wherein said recursive algorithm is configured to implement a low pass filter with an adaptive time constant or cut-off frequency.

19. A method according to claim 18 wherein estimates of magnitudes $\hat{A}(k,n)$ of said target speech components are determined from said electric input signal $Y(k,n)$ multiplied by a gain function G, where said gain function G is a function of said a posteriori signal to noise ratio estimate $\gamma(k,n)$ and said a priori target signal to noise signal ratio estimate $\zeta(k,n)$.

20. A data processing system comprising a processor and program code means for causing the processor to perform the method of claim 18.

21. A non-transitory computer readable medium storing a computer program comprising instructions which, when the program is executed by a computer, cause the computer to carry out the method of claim 18.

22. An audio processing device, comprising
- at least one input unit for providing a time-frequency representation $Y(k,n)$ of an electric input signal representing a time variant sound signal consisting of target speech signal components $S(k,n)$ from a target sound source TS and noise signal components $N(k,n)$, where k and n are frequency band and time frame indices, respectively,
- a noise reduction system configured—for each frequency band—to
    - determine a first, a posteriori, signal to noise ratio estimate $\gamma(k,n)$ of said electric input signal,
    - determine a second, a priori, target signal to noise ratio estimate $\zeta(k,n)$ of said electric input signal from said a posteriori signal to noise ratio estimate $\gamma(k,n)$ based on a recursive algorithm,
    - provide a noise reduction gain $G_{NR}$ in dependence of said a priori target signal to noise ratio estimate $\zeta(k,n)$, and
    - apply said noise reduction gain $G_{NR}$ to said electric input signal or a signal derived therefrom,
- wherein said recursive algorithm implements a low pass filter with an adaptive time constant or low-pass cut-off frequency.

23. A method of estimating an a priori signal to noise ratio $\zeta(k,n)$ of a time-frequency representation $Y(k,n)$ of an electric input signal representing a time variant sound signal consisting of target speech components and noise components, where k and n are frequency band and time frame indices, respectively, the method comprising
- determining an a posteriori signal to noise ratio estimate $\gamma(k,n)$ of said electric input signal $Y(k,n)$;
- determining an a priori target signal to noise signal ratio estimate $\zeta(k,n)$ of said electric input signal from said a posteriori signal to noise ratio estimate $\gamma(k,n)$ based on a recursive algorithm;
- providing a noise reduction gain $G_{NR}$ in dependence of said a priori target signal to noise ratio estimate $\zeta(k,n)$, and
- applying said noise reduction gain $G_{NR}$ to said electric input signal or a signal derived therefrom,
- wherein said recursive algorithm implements a low pass filter with an adaptive time constant or low-pass cut-off frequency.

* * * * *